United States Patent
Tarumi et al.

[11] Patent Number: 6,159,393
[45] Date of Patent: *Dec. 12, 2000

[54] BENZENE DERIVATIVES AND LIQUID-CRYSTALLINE MEDIUM

[75] Inventors: Kazuaki Tarumi, Seeheim; Ekkehard Bartmann, Erzhausen; Volker Reiffenrath, Rossdorf; Sabine Schoen, Darmstadt; Detlef Pauluth, Ober-Ramstadt; Brigitte Schuler, Grossostheim; Eike Poetsch, Mühltal, all of Germany

[73] Assignee: Merck Patent Gesellschaft mit Beschrankter Haftung, Germany

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/776,759

[22] PCT Filed: Jul. 31, 1995

[86] PCT No.: PCT/EP95/03045

§ 371 Date: Apr. 21, 1997

§ 102(e) Date: Apr. 21, 1997

[87] PCT Pub. No.: WO96/05159

PCT Pub. Date: Feb. 22, 1996

[30] Foreign Application Priority Data

Aug. 6, 1994 [DE] Germany ............ 44 27 932
Aug. 19, 1994 [DE] Germany ............ 44 29 280
Jan. 20, 1995 [DE] Germany ............ P9501730

[51] Int. Cl.[7] .......... C09K 19/30; C09K 19/12; C07C 19/08

[52] U.S. Cl. ............ 252/299.63; 252/299.66; 252/299.61; 570/128; 570/144

[58] Field of Search ............ 252/299.63, 299.66, 252/299.61; 570/128, 144

[56] References Cited

U.S. PATENT DOCUMENTS

| | | | |
|---|---|---|---|
| 5,308,542 | 5/1994 | Poetsch et al. | 252/299.63 |
| 5,520,846 | 5/1996 | Plach et al. | 252/299.63 |
| 5,523,127 | 6/1996 | Ohnishi et al. | 428/1 |
| 5,536,442 | 7/1996 | Reiffenrath et al. | 252/299.01 |
| 5,565,140 | 10/1996 | Hittich et al. | 252/299.63 |

*Primary Examiner*—C. H. Kelly
*Attorney, Agent, or Firm*—Millen, White, Zelano, & Branigan, P.C.

[57] ABSTRACT

A liquid-crystalline medium based on a mixture of polar compounds of positive dielectric anisotropy, characterized in that it contains one or more compounds of the general formula I

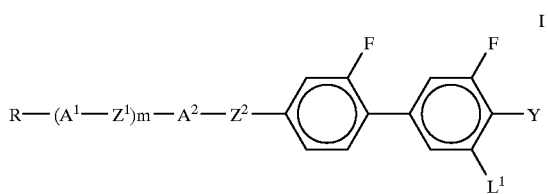

in which R, Y, $A^1$, $A^2$, $Z^1$, $Z^2$, $L^1$ and m are as defined herein.

13 Claims, No Drawings

BENZENE DERIVATIVES AND LIQUID-CRYSTALLINE MEDIUM

The present invention relates to benzene derivatives and to a liquid-crystalline medium, to the use of the latter for electrooptical purposes, and to displays containing this medium.

Liquid crystals are used, in particular, as dielectrics in display devices since the optical properties of such substances can be affected by an applied voltage. Electrooptical devices based on liquid crystals are extremely well known to those skilled in the art and may be based on various effects. Devices of this type are, for example, cells having dynamic scattering, DAP (deformation of aligned phases) cells, guest/host cells, TN cells having a twisted nematic structure, STN (super-twisted nematic) cells, SBE (super-birefringence effect) cells and OMI (optical mode interference) cells. The most common display devices are based on the Schadt-Helfrich effect and have a twisted nematic structure.

The liquid-crystal materials must have good chemical and thermal stability and good stability toward electrical fields and electromagnetic radiation. Furthermore, the liquid-crystal materials should have low viscosity and give short addressing times, low threshold voltages and high contrast in the cells.

Furthermore, they should have a suitable mesophase, for example, for the abovementioned cells, a nematic or cholesteric mesophase, at customary operating temperatures, i.e. in the broadest possible range above and below room temperature. Since liquid crystals are generally used as mixtures of a plurality of components, it is important that the components are readily miscible with one another. Further properties, such as electrical conductivity, dielectric anisotropy and optical anisotropy, must meet various requirements depending on the cell type and the area of application. For example, materials for cells having a twisted nematic structure should have positive dielectric anisotropy and low electrical conductivity.

For example, the media desired for matrix liquid-crystal displays containing integrated nonlinear elements for switching individual image points (MLC displays) are those having high positive dielectric anisotropy, broad nematic phases, relatively low birefringence, very high specific resistance, good UV and temperature stability and a low vapour pressure.

Matrix liquid-crystal displays of this type are known. Examples of nonlinear elements which can be used to switch the individual image points individually are active elements (i.e. transistors). This is then referred to as an "active matrix", and a differentiation can be made between two types:

1. MOS (Metal Oxide Semiconductor) or other diodes on a silicon wafer as substrate.
2. Thin-film transistors (TFTs) on a glass plate as substrate.

The use of monocrystalline silicon as the substrate material limits the display size since even the modular assembly of the various part displays results in problems at the joints.

In the case of the more promising type 2, which is preferred, the electrooptical effect used is usually the TN effect. A differentiation is made between two technologies: TFTs comprising compound semiconductors, such as, for example, CdSe, or TFTs based on polycrystalline or amorphous silicon. Intensive research efforts are being made worldwide in the latter technology.

The TFT matrix is applied to the inside of one glass plate of the display, while the inside of the other glass plate carries the transparent counter-electrode. Compared with the size of the image point electrode, the TFT is very small and hardly affects the image at all. This technology can also be extended to fully colour-compatible image displays, where a mosaic of red, green and blue filters is arranged in such a manner that each filter element is located opposite a switchable image element.

The TFT displays usually operate as TN cells with crossed polarizers in transmission and are illuminated from the back.

The term MLC display here covers any matrix display containing integrated nonlinear elements, i.e. in addition to the active matrix, also displays containing passive elements such as varistors or diodes (MIM=metal-insulator-metal).

MLC displays of this type are particularly suitable for TV applications (for example pocket TV sets) or for high-information displays for computer applications (laptops) and in automobile or aircraft construction. In addition to problems with respect to the angle dependency of the contrast and the switching times, problems result in MLC displays due to inadequate specific resistance of the liquid-crystal mixtures [TOGASHI, S., SEKIGUCHI, K., TANABE, H., YAMAMOTO, E., SORIMACHI, K., TAJIMA, E., WATANBE, H., SHIMIZU, H., Proc. Eurodisplay 84, September 1984: A 210–288, Matrix LCD Controlled by Double Stage Diode Rings, p. 141 ff., Paris; STROMER, M., Proc. Eurodisplay 84, September 1984: Design of Thin Film Transistors for Matrix Adressing of Television Liquid Crystal Displays, p. 145 ff., Paris]. As the resistance decreases, the contrast of an MLC display worsens and the problem of "after-image elimination" may occur. Since the specific resistance of the liquid-crystal mixture generally decreases over the life of an MLC display due to interaction with the internal surfaces of the display, a high (initial) resistance is very important to give acceptable service lives. In particular in the case of low-voltage mixtures, it was hitherto not possible to achieve very high specific resistances. It is furthermore important that the specific resistance increases as little as possible with increasing temperature and after heating and/or exposure to UV radiation. The low-temperature properties of the mixtures from the prior art are also particularly disadvantageous. It is required that crystallization and/or smectic phases do not occur, even at low temperatures, and that the temperature dependence of the viscosity is as low as possible. The MLC displays of the prior art thus do not satisfy current demands.

Thus, there continues to be a great demand for MLC displays of very high specific resistance and at the same time a broad operating temperature range, short switching times, even at low temperatures and low threshold voltage which do not have these disadvantages or only do so to a lesser extent.

For TN (Schadt-Helfrich) cells, media are desired which facilitate the following advantages in the cells:

broadened nematic phase range (in particular down to low temperatures), switchability at extremely low temperatures (outdoor use, automobiles, avionics), increased stability to UV radiation (longer life).

The media available from the prior art do not make it possible to achieve these advantages whilst simultaneously retaining the other parameters.

For supertwisted (STN) cells, media are desired which allow a greater multiplexing ability and/or lower threshold voltages and/or broader nematic phase ranges (in particular at low temperatures). To this end, a further extension of the parameter latitude available (clearing point, smectic-nematic transition or melting point, viscosity, dielectric values, elastic values) is urgently desired.

The invention has the object of providing media, in particular for MLC, TN or STN displays of this type, which do not have the abovementioned disadvantages or only do so to a lesser extent, and preferably at the same time have very high specific resistances and low threshold voltages.

It has now been found that this object can be achieved if media according to the invention are used in displays.

The invention thus relates to a liquid-crystal-line medium based on a mixture of polar compounds having positive dielectric anisotropy, characterized in that it contains one or more compounds of the general formula I

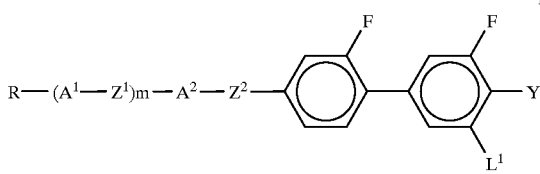

in which

R is H, an alkyl or alkenyl radical having 1 to 15 carbon atoms which is unsubstituted, monosubstituted by CN or $CF_3$ or at least monosubstituted by halogen, it also being possible for one or more $CH_2$ groups in these radicals to be replaced, in each case independently of one another, by —O—, —S—,

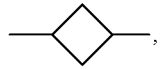

CO—, —CO—O—, —O—CO— or —O—CO—O— in such a way that O atoms are not linked directly to one another, $A^1$ and $A^2$ are each, independently of one another, a trans-1,4-cyclohexylene radical in which, in addition, one or more non-adjacent $CH_2$ groups may be replaced by —O— and/or —S—, or a cyclohexenylene radical, $Z^1$ and $Z^2$ are each, independently of one another, —CO—O—, —O—CO—, —$CH_2$O—, —O$CH_2$—, —$CH_2CH_2$—, —CH=CH—, —C≡C— or a single bond, and one of the radicals $Z^1$ and $Z^2$ is alternatively —$(CH_2)_4$— or —CH=CH—$CH_2CH_2$—, Y is F, Cl, halogenated alkyl, alkenyl or alkoxy having 1 to 6 carbon atoms, $L^1$ is H or F, and m is 0 or 1.

The compounds of the formula I have a broad range of applications. Depending on the choice of substituents, these compounds can be used as base materials from which liquid-crystalline materials are predominantly composed; however, compounds of the formula I can also be added to liquid-crystalline base materials from other classes of compounds, in order, for example, to modify the dielectric and/or optical anisotropy of a dielectric of this type and/or to optimize its threshold voltage and/or its viscosity.

In the pure state, the compounds of the formula I are colourless and form liquid-crystalline mesophases in a temperature range which is favourably located for electro-optical use. They are stable chemically, thermally and to light.

Compounds of the formula

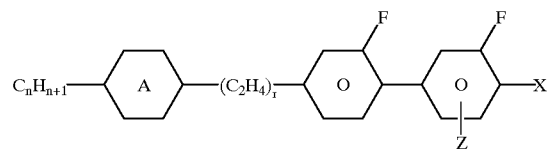

in which X is F, Cl, $CF_3$, $CHF_2$, $OCHF_2$ or $OCF_3$, r is 0 or 1, Z is H or F, and the ring A is 1,4-cyclohexylene or 1,4-phenylene have already been disclosed in WO 91-13850.

The invention also relates to the compounds of the formula I in which $L^1$ is H and the radical Y contains at least two carbon atoms.

In the media according to the invention containing compounds of the formula I, Y is preferably F, Cl, $OCF_3$, $OCHF_2$, $CF_3$, $CHFCF_3$, $CF_2CHF_2$, $C_2H_4CHF_2$, $CF_2CH_2CF_3$, $CHF_2$, $OCH_2CF_3$, $OCH_2CHF_2$, $OCF_2CHF_2$, $O(CH_2)_3CF_3$, $OCH_2C_2F_5$, $OCH_2CF_2CHF_2$, $OCH_2C_3F_7$, $OCHFCF_3$, $OC_2F_5$, $OCF_2CHFCF_3$, $OCH=CF_2$, $OCF=CF_2$, $OCF=CFCF_3$, $OCF=CF-C_2F_5$, $CH=CHF$, $CH=CF_2$, $CF=CF_2$, $CF_2OCF_3$, in particular F, $OCHFCF_3$, $OCF_3$, $OCHF_2$, $OC_2F_5$, $OC_3F_7$, $OCH=CF_2$, or $CF_2OCF_3$.

Particular preference is given to compounds of the formula I in which $L^1$ is H and/or m is 0.

$Z^1$ and $Z^2$ are preferably a single bond and —$CH_2CH_2$—, secondarily preferably —$CH_2O$—, —$OCH_2$—, —O—CO— and —CO—O—.

If one of the radicals $Z^1$ and $Z^2$ is —$(CH_2)_4$— or —CH=CH—$CH_2CH_2$—, the other radical $Z^1$ or $Z^2$ (if present) is preferably the single bond.

If R is an alkyl radical and/or an alkoxy radical, this may be straight-chain or branched. It is preferably straight-chain, has 2, 3, 4, 5, 6 or 7 carbon atoms and accordingly is preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

Oxaalkyl is preferably straight-chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, or 2-, 3-, 4-, 5-, 6-, 7-, 8- or 9-oxadecyl.

If R is an alkyl radical in which one $CH_2$ group has been replaced by —CH=CH—, this may be straight-chain or branched. It is preferably straight-chain and has 2 to 10 carbon atoms. It is accordingly in particular vinyl, prop-1- or -2-enyl, but-1-, -2- or -3-enyl, pent-1-, -2-, -3- or -4-enyl, hex-1-, -2-, -3-, -4- or -5- enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, or dec-1-, -2-, -3-, -4-, -5-, -6-, -7-, -8- or -9-enyl.

If R is an alkyl radical in which one $CH_2$ group has been replaced by —O— and one has been replaced by —CO—, these are preferably adjacent. These thus contain an acyloxy group —CO—O— or an oxycarbonyl group —O—CO—. These are preferably straight-chain and have 2 to 6 carbon atoms.

They are accordingly in particular acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl or 4-(methoxycarbonyl)butyl.

If R is an alkyl radical in which one CH$_2$ group has been replaced by unsubstituted or substituted —CH=CH— and an adjacent CH$_2$ group has been replaced by CO or CO—O or O—CO, this may be straight-chain or branched. It is preferably straight-chain and has 4 to 13 carbon atoms. It is accordingly in particular acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl or 9-methacryloyloxynonyl.

If R is an alkyl or alkenyl radical which is monosubstituted by CN or CF$_3$, this radical is preferably straight-chain. The substitution by CN or CF$_3$ is in any desired position.

If R is an alkyl or alkenyl radical which is at least monosubstituted by halogen, this radical is preferably straight-chain and halogen is preferably F or Cl. In the case of multiple substitution, halogen is preferably F. The resulting radicals also include perfluorinated radicals. In the case of monosubstitution, the fluorine or chlorine substituent may be in any desired position, but is preferably in the ω-position.

Compounds of the formula I which contain wing groups R which are suitable for polymerization reactions are suitable for the preparation of liquid-crystalline polymers.

Compounds of the formula I containing branched wing groups R may occasionally be of importance due to better solubility in the customary liquid-crystalline base materials, but in particular as chiral dopes if they are optically active. Smectic compounds of this type are suitable as components of ferroelectric materials.

Compounds of the formula I having S$_A$ phases are suitable, for example, for thermally addressed displays.

Branched groups of this type generally contain not more than one chain branch. Preferred branched radicals R are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy and 1-methylheptoxy.

If R is an alkyl radical in which two or more CH$_2$ groups have been replaced by —O— and/or —CO—O—, this may be straight-chain or branched. It is preferably branched and has 3 to 12 carbon atoms. It is accordingly in particular biscarboxymethyl, 2,2-biscarboxyethyl, 3,3-biscarboxypropyl, 4,4-biscarboxybutyl, 5,5-biscarboxypentyl, 6,6-biscarboxyhexyl, 7,7-biscarboxyheptyl, 8,8-biscarboxyoctyl, 9,9-biscarboxynonyl, 10,10-biscarboxydecyl, bis(methoxycarbonyl)methyl, 2,2-bis(methoxycarbonyl)ethyl, 3,3-bis(methoxycarbonyl)propyl, 4,4-bis(methoxycarbonyl)butyl, 5,5-bis(methoxycarbonyl)pentyl, 6,6-bis(methoxycarbonyl)hexyl, 7,7-bis(methoxycarbonyl)heptyl, 8,8-bis(methoxycarbonyl)octyl, bis(ethoxycarbonyl)methyl, 2,2-bis(ethoxycarbonyl)ethyl, 3,3-bis(ethoxycarbonyl)propyl, 4,4-bis(ethoxycarbonyl)butyl or 5,5-bis(ethoxycarbonyl)hexyl.

Preferred smaller groups of compounds of the formula I are those of the subformulae I1 to I6 [L$^1$=H or F]:

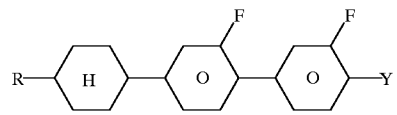

I1

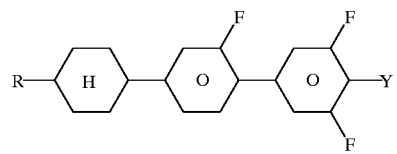

I2

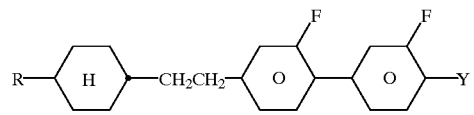

I3

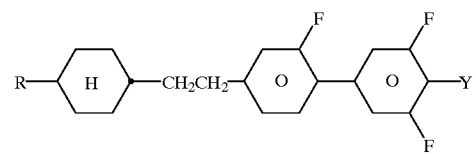

I4

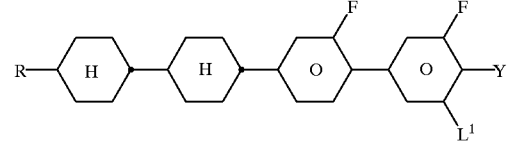

I5

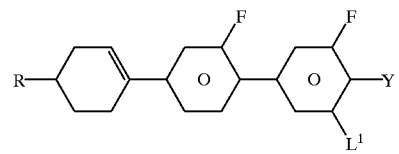

I6

Particular preference is given to the compounds of the formulae I1 and I2.

The 1,4-cyclohexenylene group preferably has the following structures:

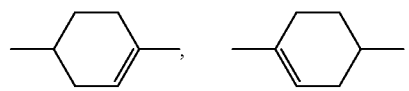

The compounds of the formula I are prepared by methods known per se, as described in the literature (for example in the standard works, such as Houben-Weyl, Methoden der Organischen Chemie, Georg-Thieme-Verlag, Stuttgart), to be precise under reaction conditions which are known and suitable for said reactions. Use may also be made here of variants which are known per se, but are not described here in greater detail.

The compounds according to the invention can be prepared, for example, by metallating a compound of formula II

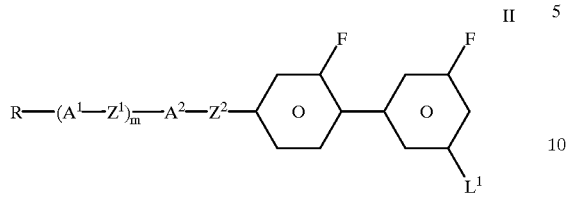

in which R, $A^1$, $A^2$, $Z^1$, $Z^2$, $L^1$ and m are as defined above, and subsequently reacting the product with a suitable electrophile, or by a coupling reaction as follows:

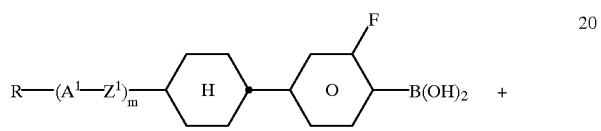

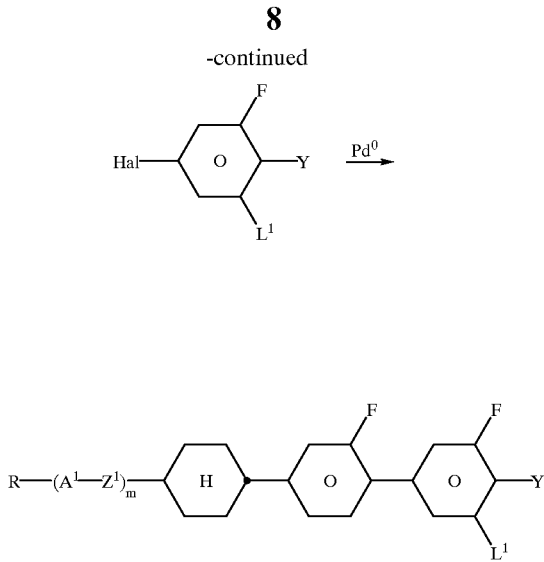

Particularly preferred compounds of the formula I are prepared, for example, as follows:

Scheme 1

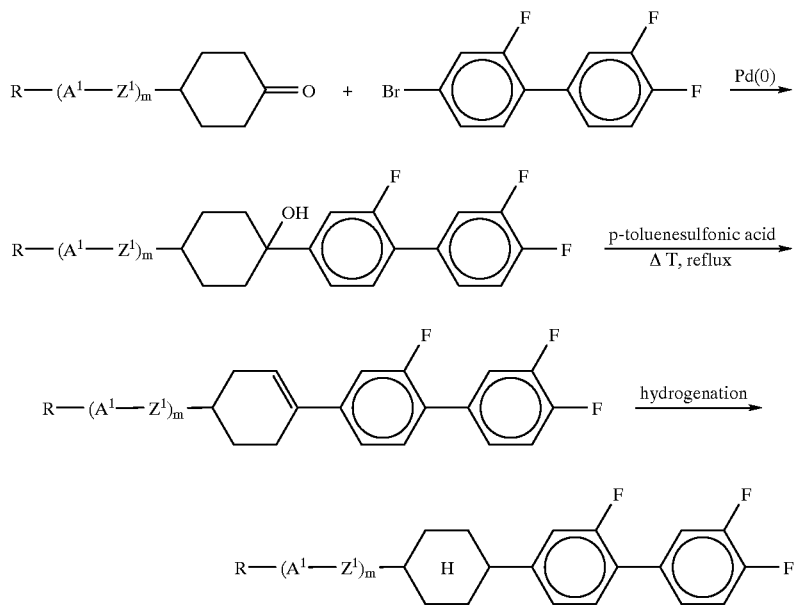

Scheme 2

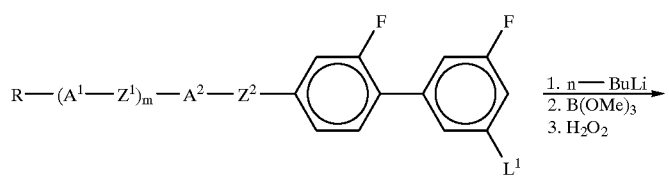

-continued
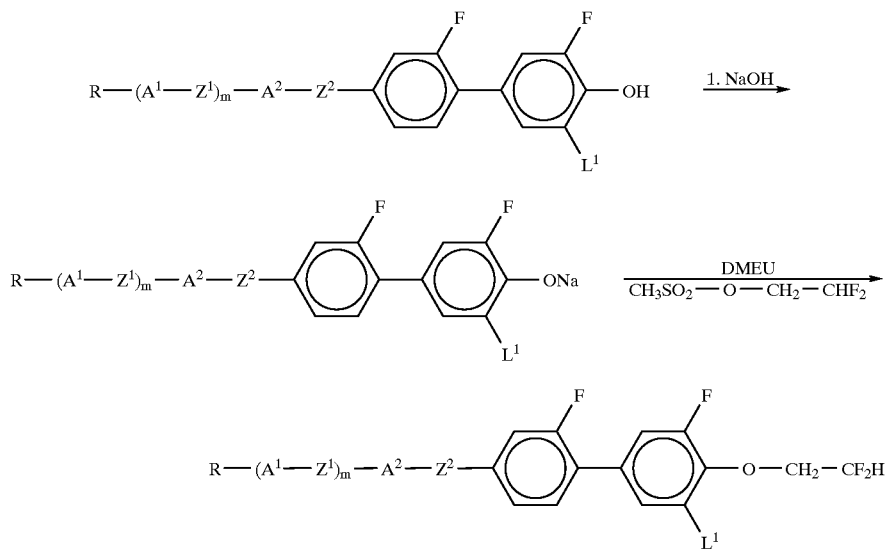
Scheme 3
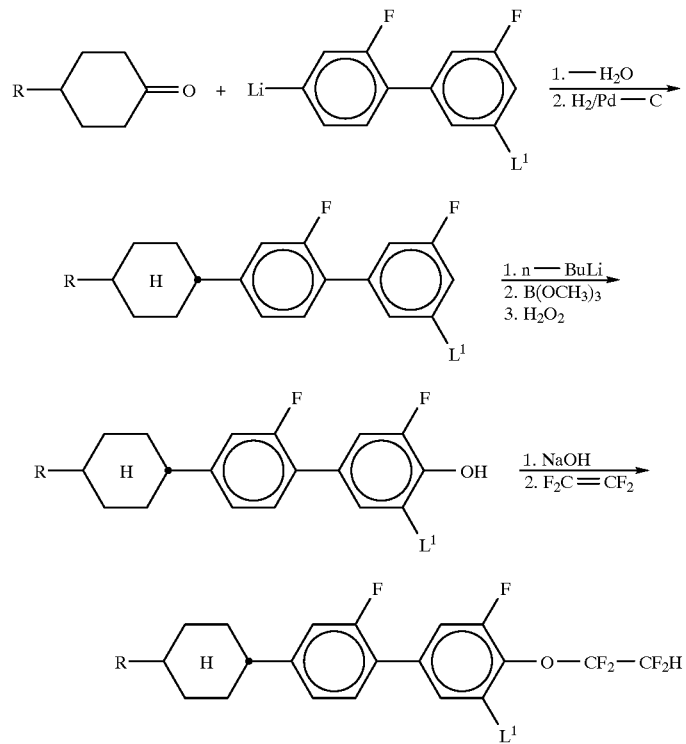

Scheme 4
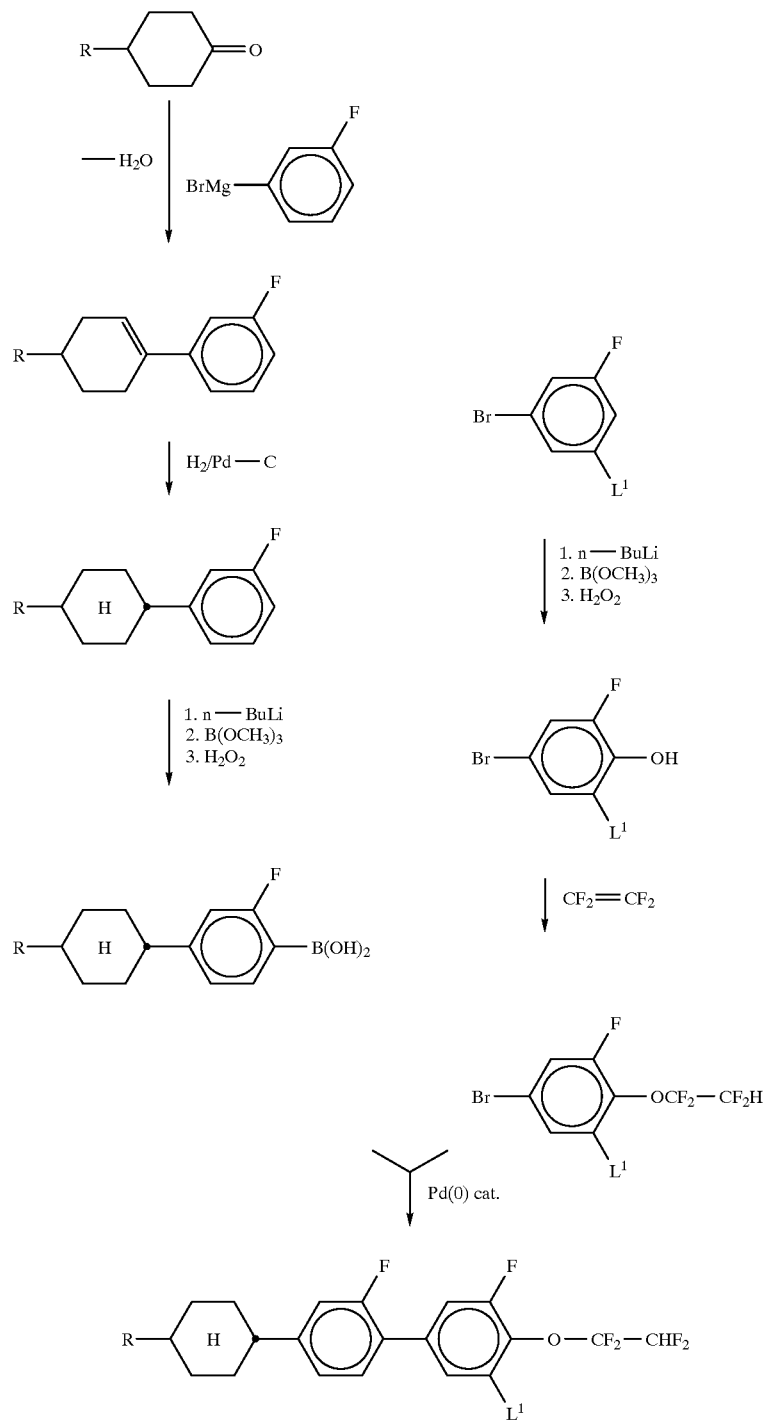

Scheme 5
(L³ = H or F)
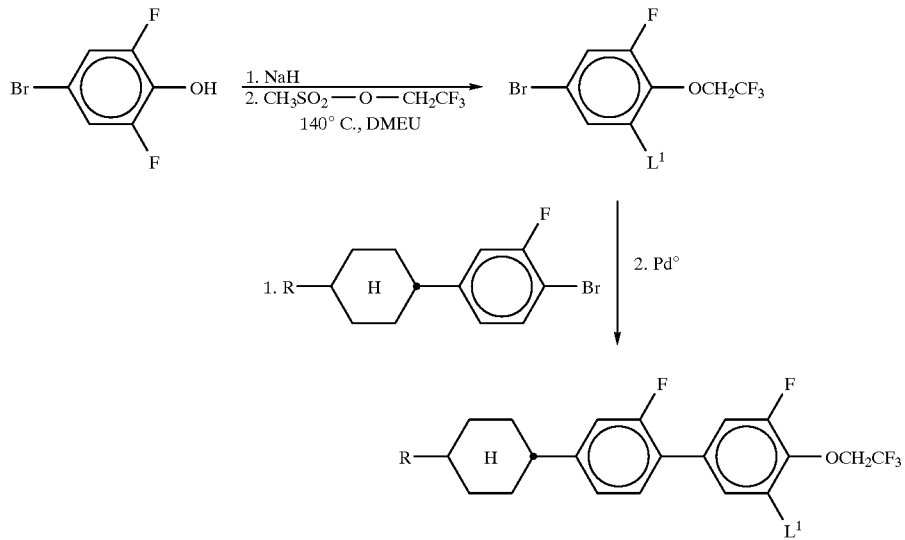
Scheme 6
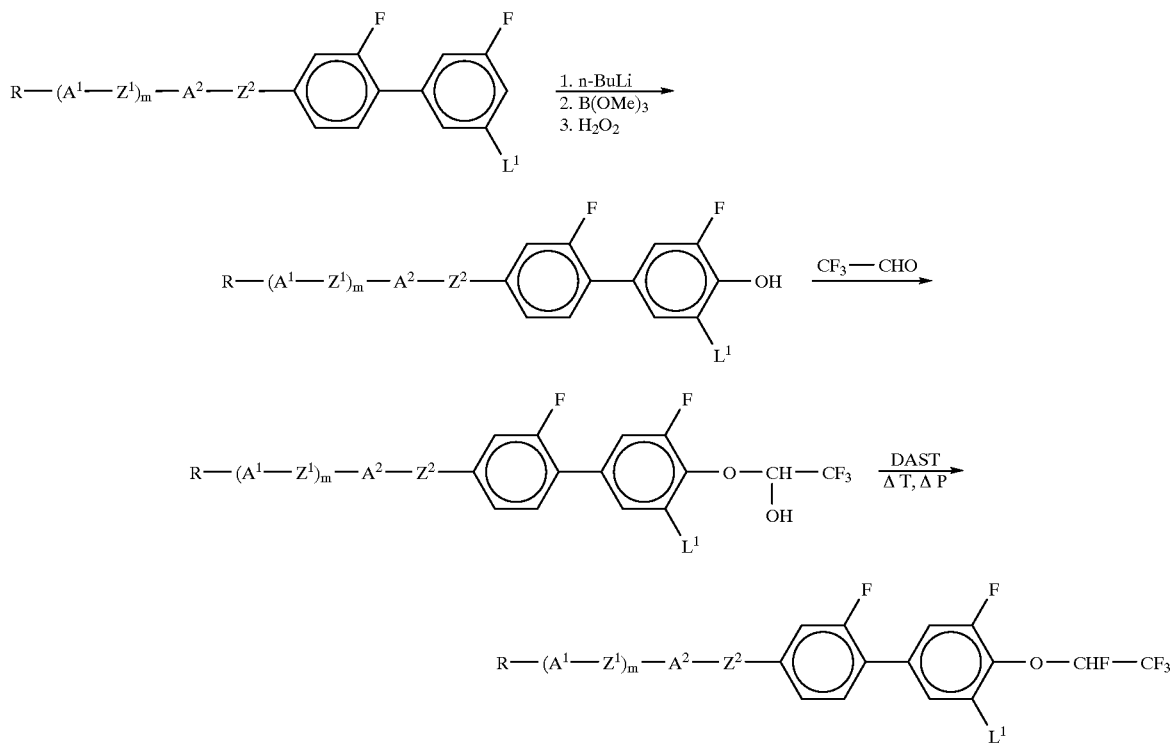

Scheme 7
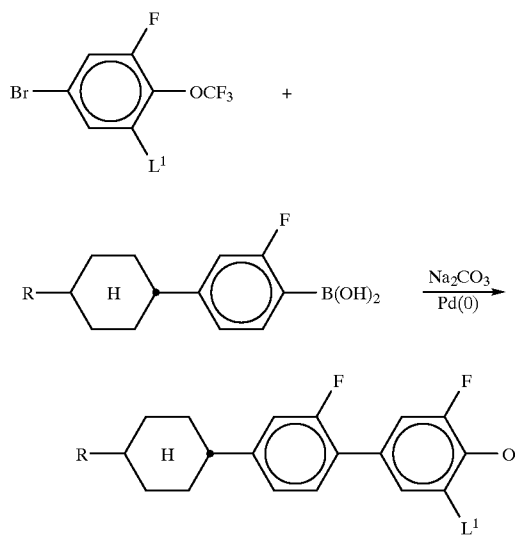
Scheme 8
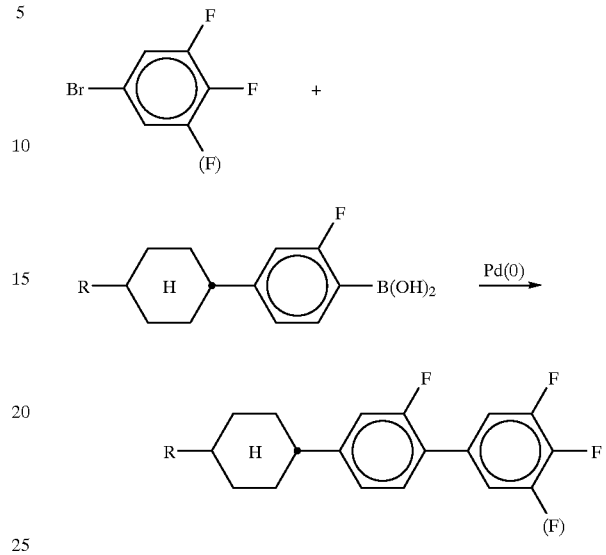
Scheme 9
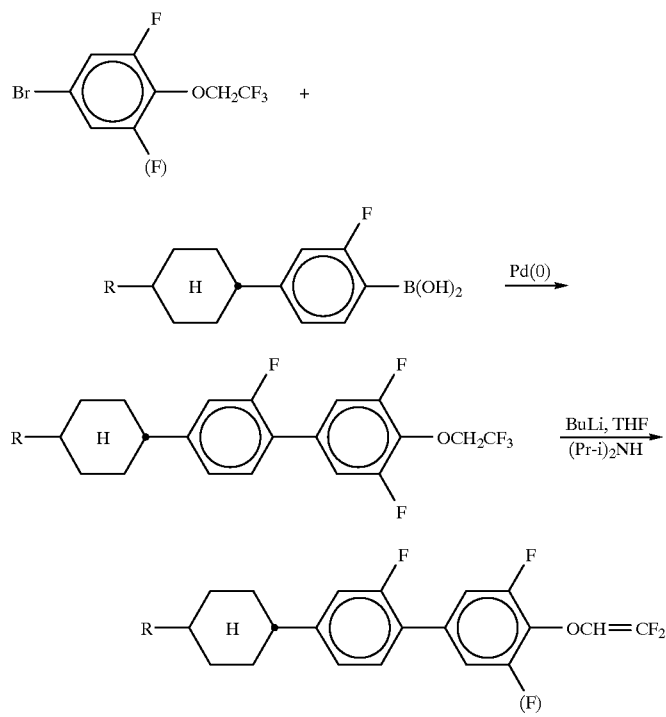
The invention also relates to electrooptical displays (in particular STN or MLC displays having two plane-parallel outer plates which, together with a frame, form a cell, integrated nonlinear elements for switching individual image points on the outer plates, and a nematic liquid-crystal mixture of positive dielectric anisotropy and high specific resistance located in the cell) which contain media of this type, and to the use of these media for electrooptical purposes.

The liquid-crystal mixtures according to the invention facilitate a significant broadening of the parameter latitude available.

The achievable combinations of clearing point, viscosity at low temperature, thermal and UV stability and dielectric anisotropy are far superior to the previous materials from the prior art.

The requirement for a high clearing point, a nematic phase at low temperature and a high Δε was previously only achievable to an unsatisfactory extent. Although systems such as, for example, ZLI-3119 have a comparable clearing point and comparatively favourable viscosities, they have, however, a Δε of only +3.

Other mixture systems have comparable viscosities and values of Δε, but only have clearing points in the region of 60° C.

The liquid-crystal mixtures according to the invention make it possible, while retaining the nematic phase at down to −20° C. and preferably down to −30° C., particularly preferably down to −40° C., to achieve clearing points above 80°, preferably above 90°, particularly preferably above 100° C., simultaneously dielectric anisotropy values Δε≧6, preferably ≧8, and a high value for the specific resistance, which means that excellent STN and MLC displays can be achieved. The mixtures are characterized in particular by low operating voltages. The TN thresholds (VIP) are below 2.0 V, preferably below 1.5 V, particularly preferably <1.3 V.

It goes without saying that a suitable choice of the components of the mixtures according to the invention also allows higher clearing points (for example above 110°) to be achieved at higher threshold voltages or lower clearing points to be achieved at lower threshold voltages while retaining the other advantageous properties. It is likewise possible to obtain mixtures of relatively high Δε and thus lower thresholds if the viscosities are increased by a correspondingly small amount. The MLC displays according to the invention preferably operate in the first transmission minimum of Gooch and Tarry [C. H. Gooch and H. A. Tarry, Electron. Lett. 10, 2–4, 1974; C. H. Gooch and H. A. Tarry, Appl. Phys., Vol. 8, 1575–1584, 1975]; in this case, a lower dielectric anisotropy in the second minimum is sufficient in addition to particularly favourable electrooptical properties, such as, for example, high gradient of the characteristic line and low angle dependency of the contrast (German Patent 30 22 818) at the same threshold voltage as in an analogous display. This allows significantly higher specific resistances to be achieved in the first minimum using the mixtures according to the invention than using mixtures containing cyano compounds. A person skilled in the art can use simple routine methods to produce the birefringence necessary for a prespecified layer thickness of the MLC display by a suitable choice of the individual components and their proportions by weight.

The viscosity at 20° C. is preferably <60 mpa.s, particularly preferably <50 mPa.s. The nematic phase range is preferably at least 90°, in particular at least 100°. This range preferably extends at least from −20° to +80°.

Measurements of the "capacity holding ratio" (HR) [S. Matsumoto et al., Liquid Crystals 5, 1320 (1989); K. Niwa et al., Proc. SID Conference, San Francisco, June 1984, p. 304 (1984); G. Weber et al., Liquid Crystals 5, 1381 (1989)] have shown that mixtures according to the invention containing compounds of the formula I exhibit a considerably smaller decrease in the HR with increasing temperature than do analogous mixtures in which the compounds of the formula I are replaced by cyanophenylcyclohexanes of the formula

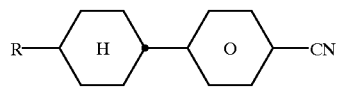

or esters of the formula

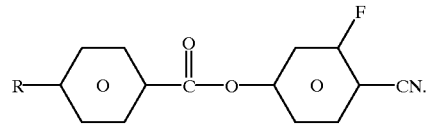

The UV stability of the mixtures according to the invention is also considerably better, i.e. they exhibit a significantly smaller decrease in the HR on exposure to UV radiation.

The media according to the invention are preferably based on a plurality (preferably two or more) of compounds of the formula I, i.e. the proportion of these compounds is 5–95%, preferably 10–60% and particularly preferably in the range 20–50%.

The individual compounds of the formulae I to XII and their subformulae which can be used in the media according to the invention are either known or can be prepared analogously to the known compounds.

Preferred embodiments are indicated below:

medium contains compounds of the formula I, wherein R is preferably ethyl, secondarily preferably propyl, butyl and pentyl. The threshold voltage of LC mixtures can be reduced in an effective manner by utilizing shorter terminal alkyl chains of polar compounds then longer ones. An ethyl chain is more effective for $V_{th}$ then a propyl or pentyl chain and this effect results from the reduction of the elastic properties.

medium additionally contains one or more compounds selected from the group comprising the general formulae II to VI:

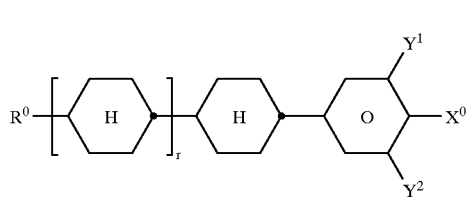

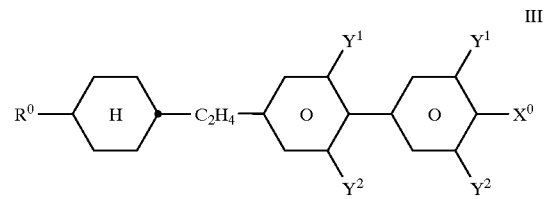

IV

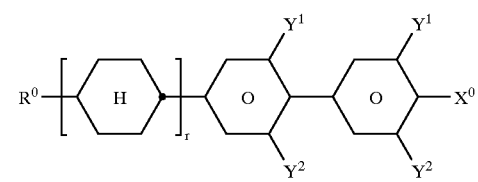

V

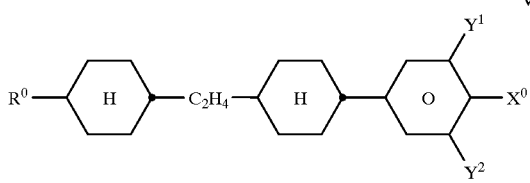

VI

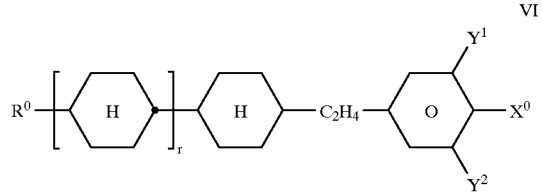

in which the individual radicals are as defined below:
R⁰: n-alkyl, oxaalkyl, fluoroalkyl or alkenyl, in each case having up to 9 carbon atoms,
X⁰: F, Cl, halogenated alkyl, alkenyl or alkoxy having 1 to 6 carbon atoms,
Y¹ and
Y²: each, independently of one another, H or F,
r: 0 or 1,
with the proviso that the compounds III and IV are not identical to the compounds of the formula I.

The compound of the formula IV is preferably

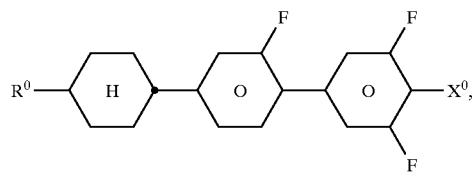

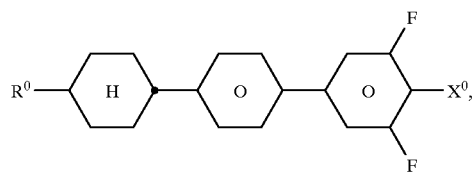

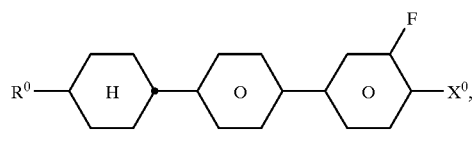

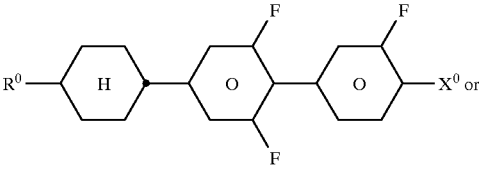

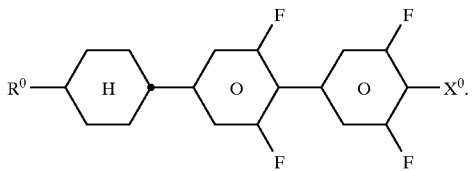

medium additionally contains one or more compounds of the formula

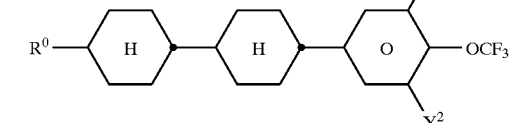

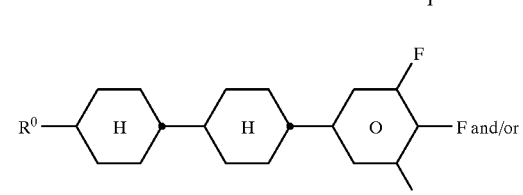

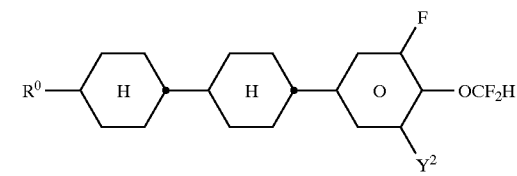

medium additionally contains one or more compounds selected from the group consisting of the general formulae VII to XII:

VII

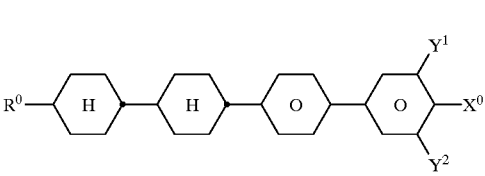

VIII

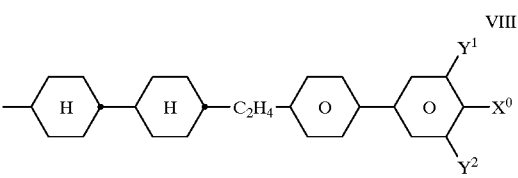

IX

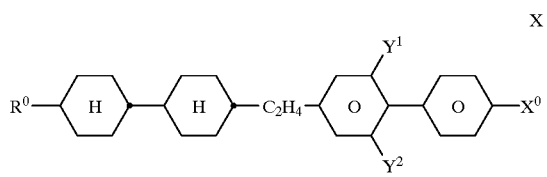

X

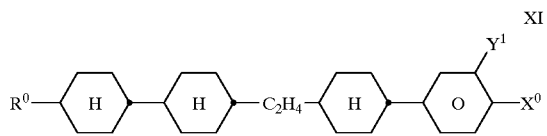

XI

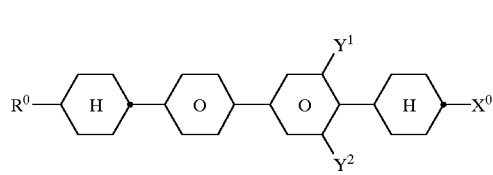

XII in which $R^0$, $X^0$, $Y^1$ and $Y^2$ are each, independently of one another, as defined in claim 2, preferably is F, Cl, $CF_3$, $OCF_3$, $OCHF_2$, alkyl, oxaalkyl, fluoroalkyl or alkenyl, in each case having up to 6 carbon atoms.

the proportion of compounds of the formulae I to VI together in the total mixture is at least 50% by weight the proportion of compounds of the formula I in the total mixture is from 10 to 50% by weight the proportion of compounds of the formulae II to VI in the total mixture is from 30 to 70% by weight

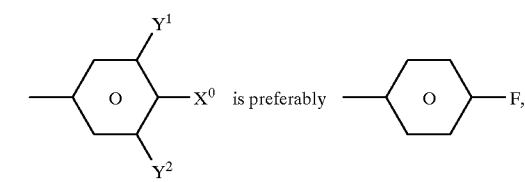

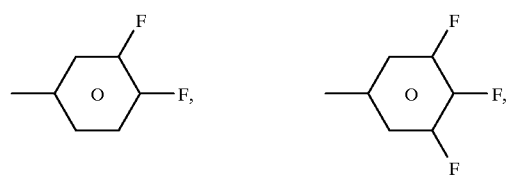

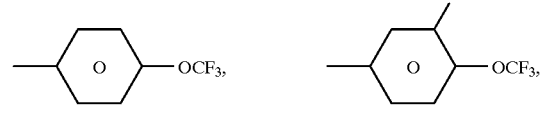

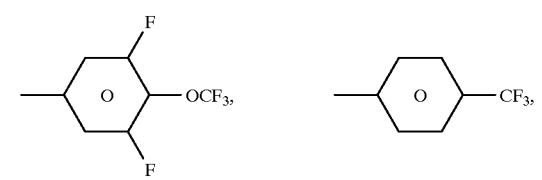

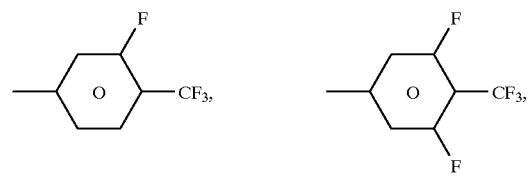

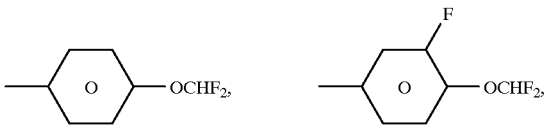

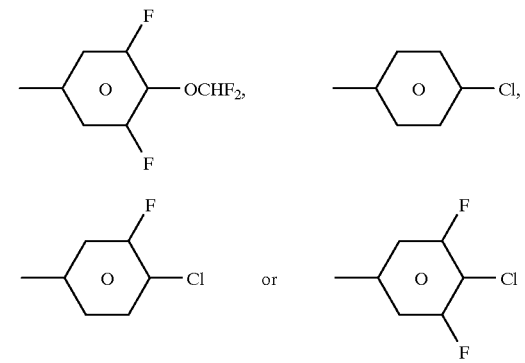

the medium contains compounds of the formulae II, III, IV, V or VI $R^0$ is straight-chain alkyl or alkenyl having 2 to 7 carbon atoms the medium essentially comprises compounds of the formulae I to VI the medium contains further compounds, preferably selected from the following group consisting of the general formulae XIII to XVI:

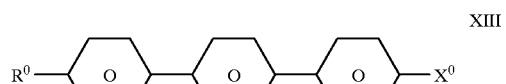

XIII

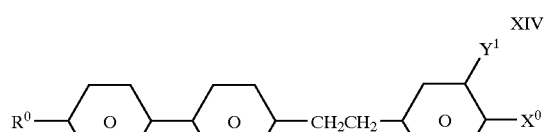

XIV

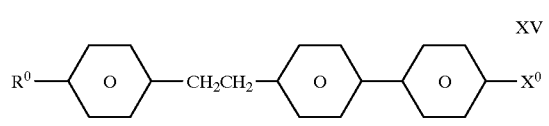

XV

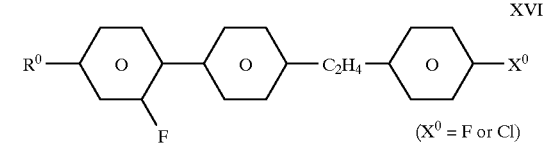

XVI ($X^0$ = F or Cl)

in which $R^0$ and $X^0$ are as defined above and the 1,4-phenylene rings may be substituted by CN, chlorine or fluorine. The 1,4-phenylene rings are preferably mono- or polysubstituted by fluorine atoms.

the I:(II+III+IV+V+VI) weight ratio is preferably from 1:10 to 10:1.

medium essentially comprises compounds selected from the group consisting of the general formulae I to XII.

It has been found that even a relatively small proportion of compounds of the formula I mixed with conventional liquid-crystal materials, but in particular with one or more compounds of the formula II, III, IV, V and/or VI, results in a significant lowering of the threshold voltage and in low values for the birefringence, and at the same time broad nematic phases with low smectic-nematic transition temperatures are observed, as a result of which the shelf life is improved. The compounds of the formulae I to VI are colourless, stable and readily miscible with one another and with other liquid-crystal materials.

The term "alkyl" covers straight-chain and branched alkyl groups having 1–7 carbon atoms, in particular the straight-chain groups methyl, ethyl, propyl, butyl, pentyl, hexyl and heptyl. Groups having 2–5 carbon atoms are generally preferred.

The term "alkenyl" covers straight-chain and branched alkenyl groups having 2–7 carbon atoms, in particular the straight-chain groups. Preferred alkenyl groups are $C_2$–$C_7$-1E-alkenyl, $C_4$–$C_7$-3E-alkenyl, $C_5$–$C_7$-4-alkenyl, $C_6$–$C_7$-5-alkenyl and $C_7$-6-alkenyl, in particular $C_2$–$C_7$-1E-alkenyl, $C_4$–$C_7$-3E-alkenyl and $C_5$–$C_7$-4-alkenyl. Examples of preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are generally preferred.

The term "fluoroalkyl" preferably covers straight-chain groups containing terminal fluorine, i.e. fluoromethyl, 2-fluoroethyl, 3-fluoropropyl, 4-fluorobutyl, 5-fluoropentyl, 6-fluorohexyl and 7-fluoroheptyl. However, other positions of the fluorine are not excluded.

The term "oxaalkyl" preferably covers straight-chain radicals of the formula $C_nH_{2n+1}$—O—$(CH_2)_m$, in which n and m are each, independently of one another, from 1 to 6. n is preferably 1 and m is preferably from 1 to 6.

Through a suitable choice of the meanings of $R^0$ and $X^0$, the addressing times, the threshold voltage, the gradient of the transmission characteristic lines, etc., can be modified as desired. For example, 1E-alkenyl radicals, 3E-alkenyl radicals, 2E-alkenyloxy radicals and the like generally give shorter addressing times, improved nematic tendencies and a higher ratio between the elastic constants $k_{33}$ (bend) and $k_{11}$ (splay) compared with alkyl and alkoxy radicals. 4-Alkenyl radicals, 3-alkenyl radicals and the like generally give lower threshold voltages and lower values of $k_{33}/k_{11}$ compared with alkyl and alkoxy radicals.

A —$CH_2CH_2$— group in $Z^2$ generally results in higher values of $k_{33}/k_{11}$ compared with a simple covalent bond. Higher values of $k_{33}/k_{11}$ facilitate, for example, flatter transmission characteristic lines in TN cells with a 90° twist (for achieving grey tones) and steeper transmission characteristic lines in STN, SBE and OMI cells (greater multiplexing ability), and vice versa.

The optimum mixing ratio of the compounds of the formulae I and II+III+IV+V+VI depends substantially on the desired properties, on the choice of the components of the formulae I, II, III, IV, V and/or VI and on the choice of any other components which may be present. Suitable mixing ratios within the abovementioned range can easily be determined from case to case.

The total amount of compounds of the formulae I to XII in the mixtures according to the invention is not crucial. The mixtures may therefore contain one or more further components in order to optimize various properties. However, the effect observed on the addressing times and the threshold voltage is generally greater the higher the total concentration of compounds of the formulae I to XII.

In a particularly preferred embodiment, the media according to the invention contain compounds of the formulae II to VI (preferably II and/or III) in which $X^0$ is $OCF_3$, $OCHF_2$, F, $OCH=CF_2$, $OCF=CF_2$ or $OCF_2$—$F_2H$. A favourable synergistic effect with the compounds of the formula I results in particularly advantageous properties.

The construction of the MLC display according to the invention from polarizers, electrode baseplates and electrodes with surface treatment corresponds to the construction which is conventional for displays of this type. The term conventional construction here is widely drawn and also covers all derivatives and modifications of the MLC display, in particular also matrix display elements based on poly-Si TFTs or MIMs.

An essential difference between the displays according to the invention and those customary hitherto based on the twisted nematic cell is, however, the choice of liquid-crystal parameters in the liquid-crystal layer.

The liquid-crystal mixtures which can be used according to the invention are prepared in a manner which is conventional per se. In general, the desired amount of the components used in the lesser amount is dissolved in the components making up the principal constituents, expediently at elevated temperature. It is also possible to mix solutions of the components in an organic solvent, for example in acetone, chloroform or methanol, and, after thorough mixing, to remove the solvent again, for example by distillation.

The dielectrics may also contain other additives known to those skilled in the art and described in the literature. For example, 0–15% of pleochroic dyes or chiral dopes can be added.

C denotes a crystalline phase, S a smectic phase, $S_c$ a smectic C phase, N a nematic phase and I the isotropic phase.

$V_{10}$ denotes the voltage for 10% transmission (view angle perpendicular to the plate surface). $t_{on}$ denotes the switch-on time and $t_{off}$ the switch-off time at an operating voltage corresponding to 2.5 times the value of $V_{10}$. Δn denotes the optical anisotropy and $n_0$ the refractive index. Δε denotes the dielectric anisotropy (Δε=$ε_∥$–$ε_{195}$, where $ε_{81}$ is the dielectric constant parallel to the longitudinal molecular axes and $ε_⊥$ is the dielectric constant perpendicular thereto). The electrooptical data were measured in a TN cell at the 1st minimum (i.e. at a d·Δn value of 0.5) at 20° C., unless expressly stated otherwise. The optical data were measured at 20° C., unless expressly stated otherwise.

In the present application and in the examples below, the structures of the liquid-crystal compounds are indicated by acronyms, with the transformation into chemical formulae taking place in accordance with Tables A and B below. All radicals $C_nH_{2n+1}$ and $C_mH_{2m+1}$ are straight-chain alkyl radicals containing n or m carbon atoms. The coding in Table B is self-evident. In Table A, only the acronym for the base structure is given. In individual cases, the acronym for the base structure is followed, separated by a hyphen, by a code for the substituents $R^1$, $R^2$, $L^1$ and $L^2$:

| Code for $R^1$, $R^2$, $L^1$, $L^2$ | $R^1$ | $R^2$ | $L^1$ | $L^2$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | H | F |
| nF | $C_nH_{2n+1}$ | F | H | H |
| nOF | $OC_nH_{2n+1}$ | F | H | H |
| nCl | $C_nH_{2n+1}$ | Cl | H | H |
| nF.F | $C_nH_{2n+1}$ | F | H | F |
| nF.F.F | $C_nH_{2n+1}$ | F | F | F |
| nCF$_3$ | $C_nH_{2n+1}$ | CF$_3$ | H | H |
| nOCF$_3$ | $C_nH_{2n+1}$ | OCF$_3$ | H | H |
| nOCF$_2$ | $C_nH_{2n+1}$ | OCHF$_2$ | H | H |
| nS | $C_nH_{2n+1}$ | NCS | H | H |
| rVsN | $C_rH_{2r+1}$—CH=CH—$C_sH_{2s}$— | CN | H | H |
| rEsN | $C_rH_{2r+1}$—O—$C_sH_{2s}$— | CN | H | H |
| nAm | $C_nH_{2n+1}$ | $COOC_mH_{2m+1}$ | H | H |
| nOCCF$_2$.F.F | $C_nH_{2n+1}$ | $OCH_2CF_2H$ | F | F |

Preferred mixture components are shown in Tables A and B.

TABLE A

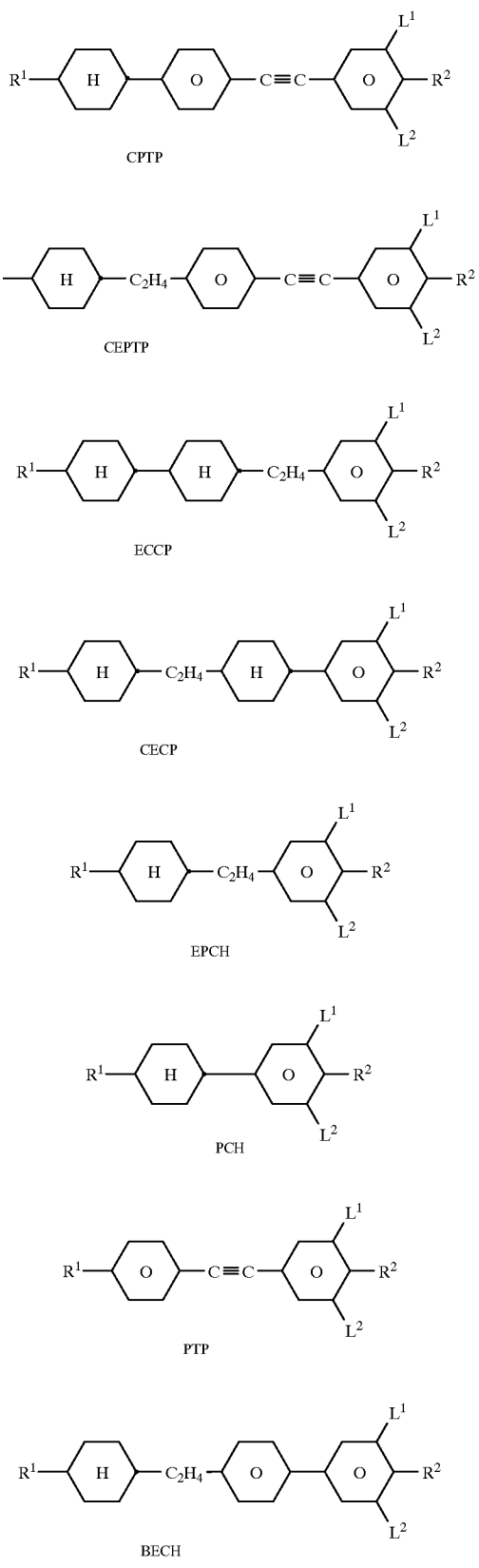

TABLE A-continued
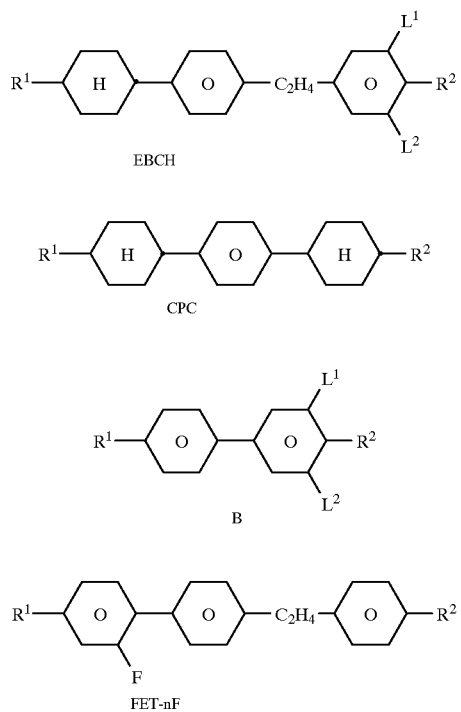
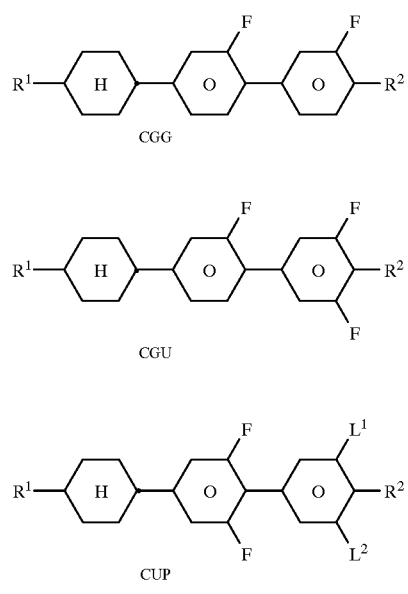
TABLE B
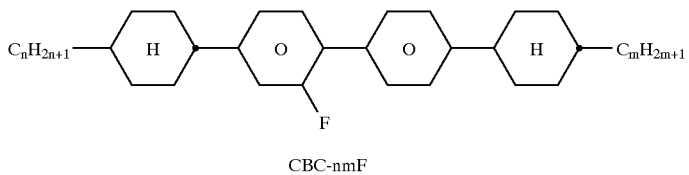
CBC-nmF
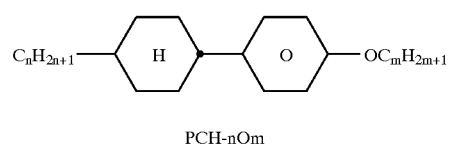
PCH-nOm
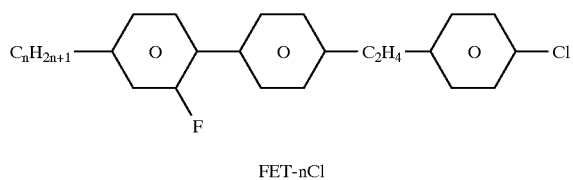
FET-nCl
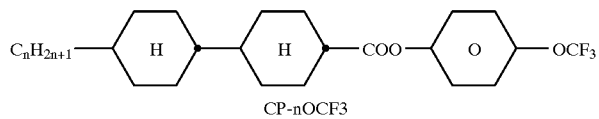
CP-nOCF3

TABLE B-continued
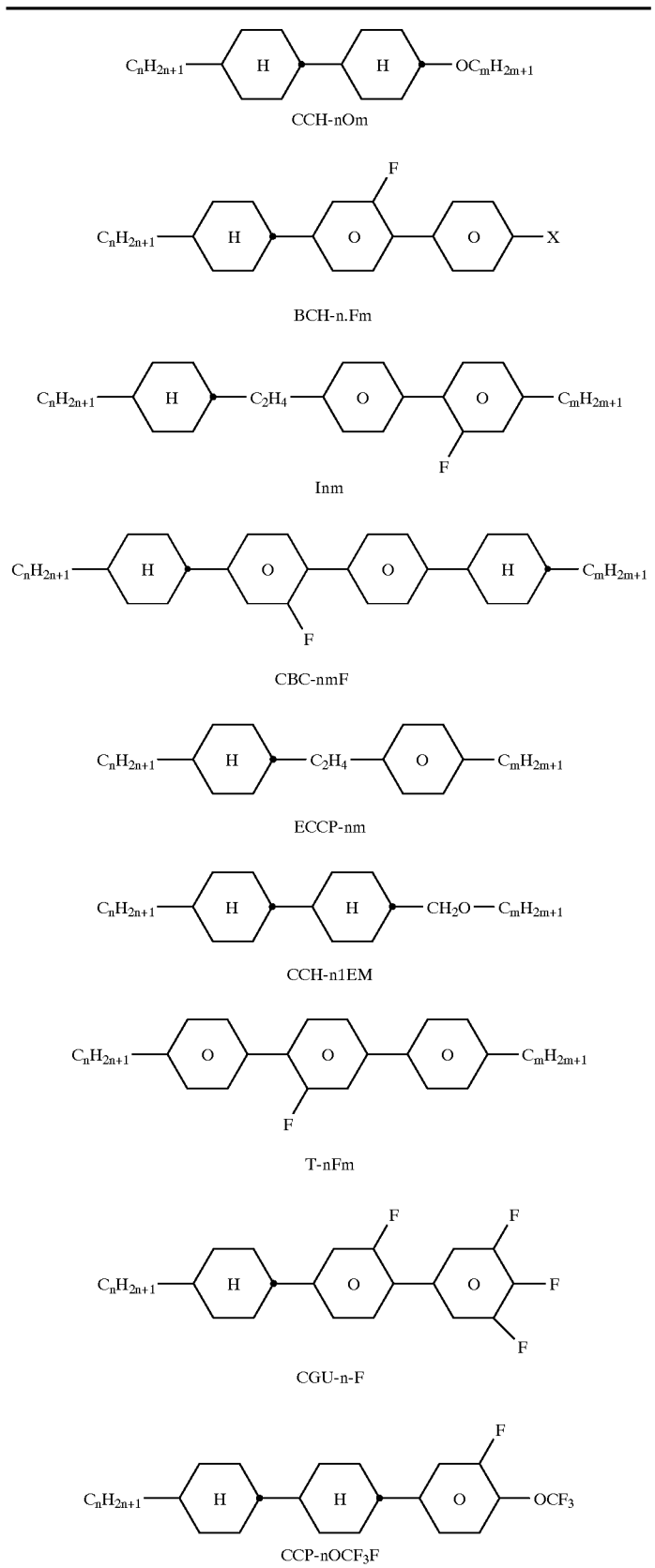

TABLE B-continued

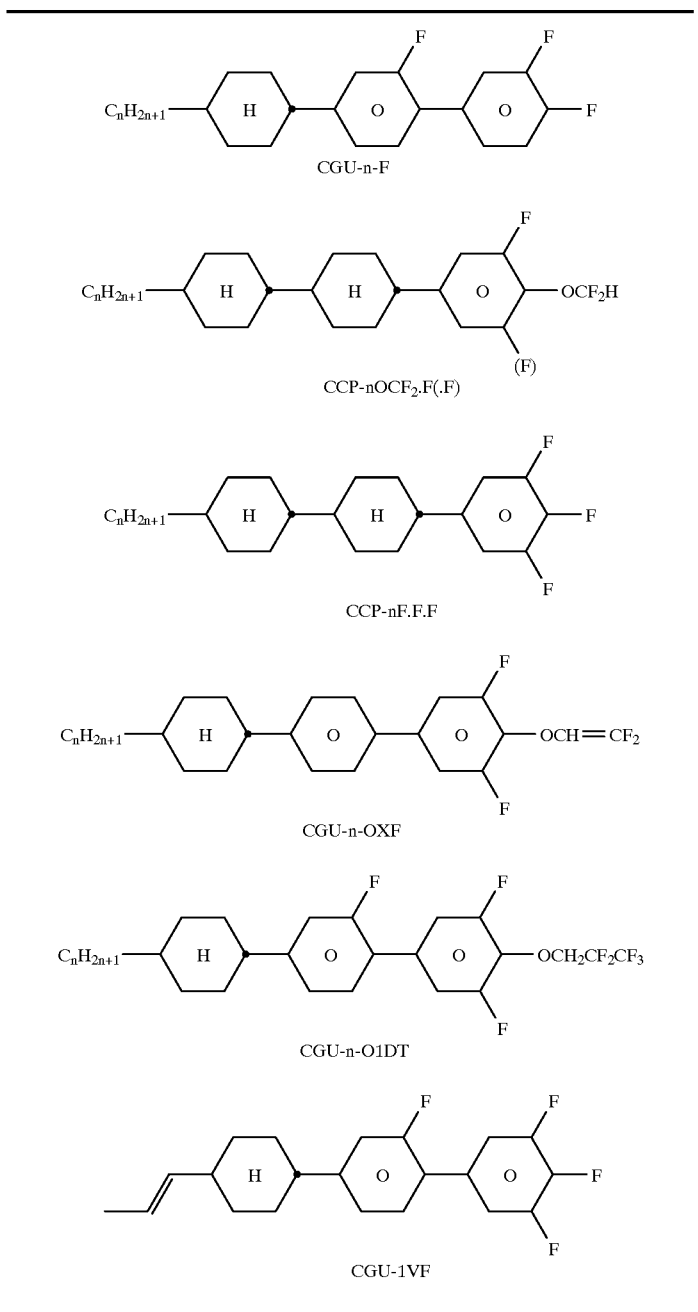

The examples below are intended to illustrate the invention without presenting a limitation. Above and below, percentages are by weight. All temperatures are given in degrees Celsius. m.p. denotes melting point, c.p.=clearing point. Furthermore, C=crystalline state, N=nematic phase, S=smectic phase and I=isotropic phase. The numbers between these symbols represent the transition temperatures. Δn denotes optical anisotropy (589 nm, 20° C.) and the viscosity (mm$^2$/sec) was determined at 20° C.

"Conventional work-up" means that, if necesary, water is added, the mixture is extracted with dichloromethane, diethyl ether, methyl tert-butyl ether or toluene, the organic phase is separated off, dried and evaporated, and the product is purified by distillation under reduced pressure or crystallization and/or chromatography. The following abbreviations are used:

| | |
|---|---|
| DMEU | 1,3-dimethyl-2-imidazolidinone |
| POT | potassium tertiary-butoxide |
| THF | tetrahydrofuran |
| pTSOH | p-toluenesulphonic acid |

EXAMPLE 1

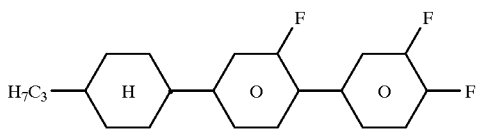

Step 1.1

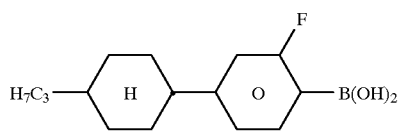

1.32 mol of n-butyllithium (15% in n-hexane) are added dropwise over the course of 1 hour at −100° C. in a nitrogen atmosphere to 1.2 mol of 4-(trans-4-propylcyclohexyl)-2-fluorobenzene, 1.2 mol of potassium tert-butoxide and 3 l of THF. The mixture is stirred for a further 1 hour, and 1.38 mol of trimethyl borate are added dropwise to the reaction mixture at −100° C., and the mixture is stirred for a further 1.5 hours. 3.6 l of 18% HCl are added, the organic phase is separated off, and the aqueous phase is extracted with toluene. The combined organic extracts are subsequently subjected to a conventional work-up.

Step 1.2

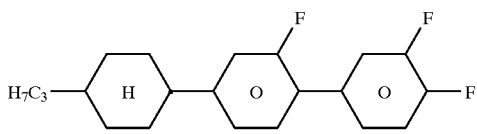

1.6 g of tetrakis(triphenylphosphine)palladium-(0) and a sodium carbonate solution (41.66 g of $Na_2CO_3$ in 150 ml of $H_2O$) are added to 0.13 mol of 4-(trans-4-propylcyclohexyl)-2-fluorophenylboronic acid, 0.13 mol of 2,3,4-trifluorobromobenzene, 325 ml of toluene and 130 ml of ethanol. The mixture is allowed to cool to room temperature, and the organic phase is separated off. The aqueous phase is extracted with toluene, and the combined organic extracts are subsequently subjected to conventional work-up. C 42 N 57.1 I; Δn+0.131; Δε=10.01.

The following compounds of the formula

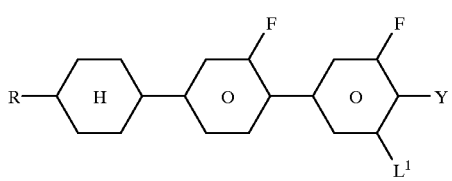

are prepared analogously:

| R | Y | L$^1$ | |
|---|---|---|---|
| CH$_3$ | F | H | |
| CH$_3$ | F | F | |
| C$_2$H$_5$ | F | H | C 36 N (−1,9) I; Δn = +0,112; Δε = 8,86 |
| C$_2$H$_5$ | F | F | C 55 I; Δn = +0,104; Δε = 15,03 |
| n-C$_3$H$_7$ | F | F | C 64 I; Δn = +0,117; Δε = 14,02 |
| n-C$_5$H$_{11}$ | F | H | C 35 N 73,9 I; Δn = +0,124; Δε = 9,68 |
| n-C$_5$H$_{11}$ | F | F | C 63 N (37.0) I; Δn = +0,114; Δε = 13,76 |
| n-C$_6$H$_{13}$ | F | H | |
| n-C$_6$H$_{13}$ | F | F | |
| n-C$_3$H$_7$ | Cl | H | |
| n-C$_3$H$_7$ | Cl | F | |
| n-C$_5$H$_{11}$ | Cl | H | C 66 N 112,1 I; Δn = +0,166; Δε = 11,19 |
| n-C$_5$H$_{11}$ | Cl | F | |

EXAMPLE 2

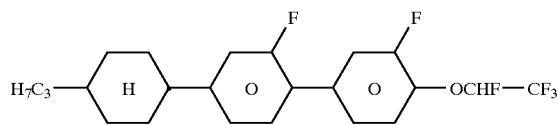

Step 2.1

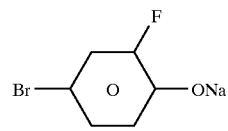

1.0 mol of sodium hydride (60%) is suspended in 200 ml of THF under nitrogen, and 1.0 mol of 4-bromo-2-fluorophenol, dissolved in 400 ml of THF, is added dropwise at 0° C. The mixture is allowed to warm to room temperature, stirred for 0.5 hour and filtered. The filtrate is evaporated, dissolved in toluene and evaporated to induce crystallization. The residue is precipitated using petroleum ether. The crystals are filtered off with suction and dried.

Step 2.2

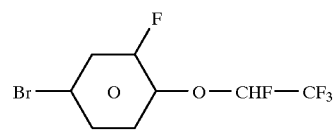

0.08 mol of the phenoxide from 2.1 is introduced into 80 ml of DMEU, and the mixture is heated to 50° C. 0.088 mol of 1,2,2,2-tetrafluoro-1-iodoethane is added, and the mixture is stirred at 50° C. for 16 hours. The mixture is allowed to cool to room temperature and water is added. The mixture is acidified using dilute HCl, extracted with methyl tert-butyl ether, then with 10% NaOH and water, dried over $Na_2SO_4$ and filtered. The filtrate is evaporated and distilled at 800 mbar in a bulb tube.

Step 2.3

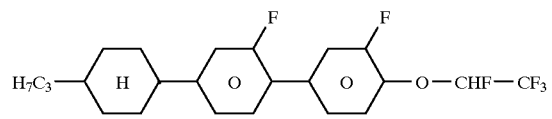

0.013 mol of 1-(1,2,2,2-tetrafluoroethoxy)-2-fluoro-4-bromobenzene are dissolved in 50 ml of THF, the solution is heated to 60° C., and 0.012 mol of 4-(trans-4-propylcyclohexyl)-2-fluorophenylboronic acid and a solution comprising 0.013 mol of $KH_2PO_4$, 0.025 mol of $Na_2HPO_4$ and 25 ml of water are added. 0.012 mol of tetrakis(triphenylphosphine)palladium(0) is added, and the mixture is stirred at 70° C. overnight. The mixture is allowed to cool to room temperature and is subjected to conventional work-up. C 15 N 103.2 I; Δn=0.128; Δε=16.78

The following compounds of the formula

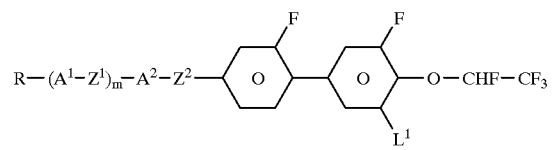

are prepared analogously:

| R | -(A$^1$ – Z$^1$)$_m$-A$^2$ – Z$^2$- | L$^1$ | |
|---|---|---|---|
| C$_2$H$_5$ | 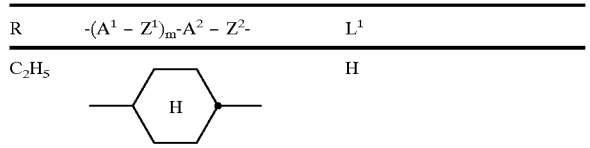 | H | |
| C$_2$H$_5$ |  | F | C 52 N (50.0) I; Δn = +0.117; Δε =20.18 |
| n-C$_3$H$_7$ | 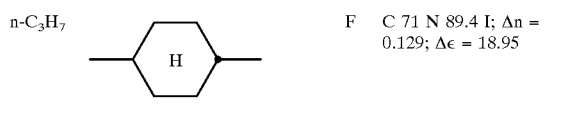 | F | C 71 N 89.4 I; Δn = 0.129; Δε = 18.95 |
| n-C$_4$H$_9$ |  | H | |
| n-C$_4$H$_9$ |  | F | |
| n-C$_5$H$_{11}$ |  | H | |
| n-C$_5$H$_{11}$ | 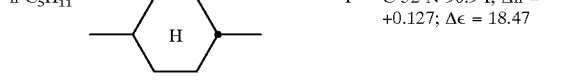 | F | C 52 N 96.9 I; Δn = +0.127; Δε = 18.47 |

-continued

| R | -(A$^1$ – Z$^1$)$_m$-A$^2$ – Z$^2$- | L$^1$ |
|---|---|---|
| n-C$_6$H$_{13}$ | 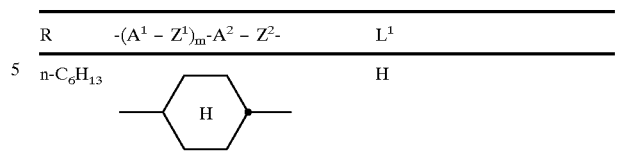 | H |
| n-C$_6$H$_{13}$ | 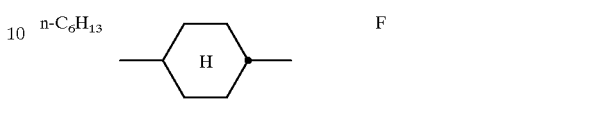 | F |
| C$_2$H$_5$ | 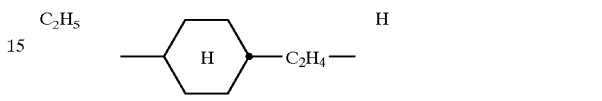 | H |
| C$_2$H$_5$ | 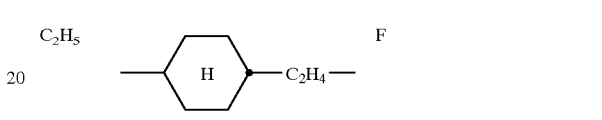 | F |
| n-C$_3$H$_7$ | 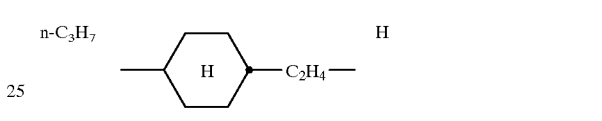 | H |
| n-C$_3$H$_7$ | 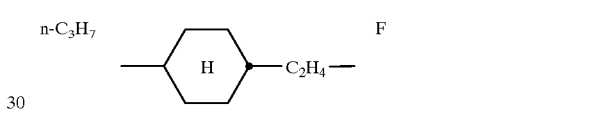 | F |
| n-C$_5$H$_{11}$ | 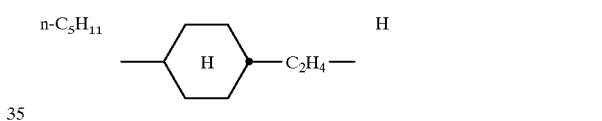 | H |
| n-C$_5$H$_{11}$ | 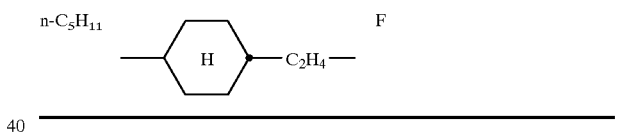 | F |

EXAMPLE 3

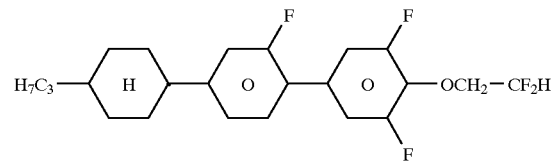

Step 3.1

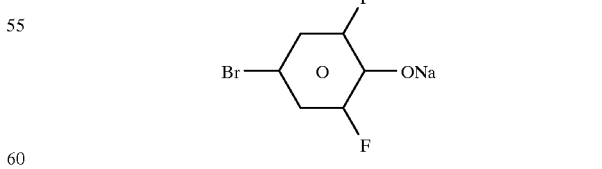

Under a nitrogen atmosphere, 0.05 mol of sodium 1-bromo-3,5-difluorophenoxide is introduced into 50 ml of DMEU, and the mixture is heated to 50° C. 0.05 ml of 1-bromo-2,2-difluoroethane is added dropwise with stirring. The mixture is subsequently stirred at 50° C. overnight. 0.005 mol of 1-bromo-2,2-difluoroethane is added, and the mixture is stirred at 70° C. for a further 24 hours. The mixture is allowed to cool to room temperature, water is added, and the mixture is subjected to conventional work-up.

Step 3.2

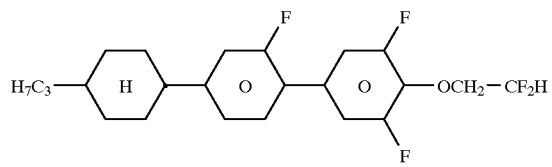

0.03 mol of p-trans-[4-propylcyclohexyl]-2-fluorophenylboronic acid in 60 ml of toluene is added to 4.8 g of NaOH in 30 ml of water, and the mixture is stirred at 45° C. for 0.5 hour. 0.03 mol of 1-(2,2-difluoroethoxy)-4-bromo-2,6-difluorobenzene and 0.7 g of tetrakis(triphenylphosphine)palladium(0) are added to the solution, and the mixture is stirred at 100° C. overnight. The mixture is cooled to room temperature, and the organic phase is separated off. The solvent is removed in a rotary evaporator, and the residue is filtered through a silica gel fritt with petroleum ether 50–70°. The filtrate is evaporated, and the residue is crystallized from n-hexane. C 56 N 97.2 I; Δn=+0.139; Δε=12.34

The following compounds of the formula

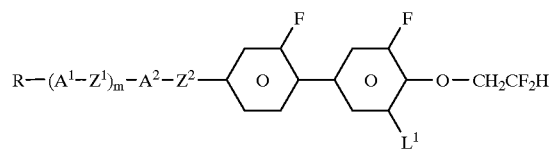

are prepared analogously:

| R | —(A¹ – Z¹)ₘ-A² – Z²- | L¹ |
|---|---|---|
| C₂H₅ | cyclohexyl | H |
| C₂H₅ | cyclohexyl | F |
| n-C₃H₇ | cyclohexyl | H |
| n-C₄H₉ | cyclohexyl | H |
| n-C₄H₉ | cyclohexyl | F |

| R | —(A¹ – Z¹)ₘ-A² – Z²- | L¹ | |
|---|---|---|---|
| n-C₅H₁₁ | cyclohexyl | H | |
| n-C₅H₁₁ | cyclohexyl | F | C 35 N 102.5 I; Δn = +0.136; Δε = 11.07 |
| n-C₆H₁₃ | cyclohexyl | H | |
| n-C₆H₁₃ | cyclohexyl | F | |
| n-C₃H₇ | cyclohexyl—C₂H₄— | H | |
| n-C₃H₇ | cyclohexyl—C₂H₄— | F | |
| n-C₅H₁₁ | cyclohexyl—C₂H₄— | H | |
| n-C₅H₁₁ | cyclohexyl | F | |

EXAMPLE 4

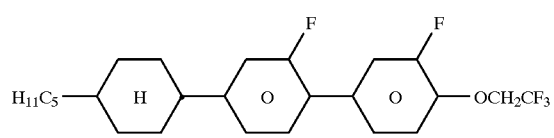

Step 4.1

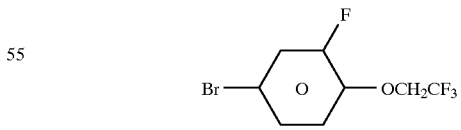

0.085 mol of sodium 4-bromo-2-fluorophenoxide is dissolved in 100 l of 1,3-dimethyl-2-imidazolidinone, the solution is heated to 140° C., and 0.09 mol of 2,2,2-trifluoroethyl methanesulphonate is added dropwise. The solution is stirred at 140° C. for 24 hours. 500 ml of ice water are subsequently added, and the mixture is subjected to conventional work-up.

Step 4.2

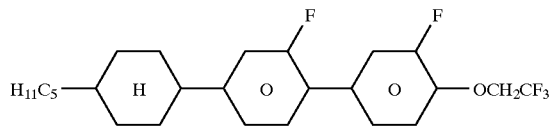

0.05 mol of trans-n-pentylcyclohexyl-2-fluorophenylboronic acid, 20 ml of toluene, 10 ml of ethanol, 0.030 mol of $Na_2CO_3$ and 0.86 mol of tetrakis(triphenylphosphine)palladium(0) are added to 0.015 mol of 4-bromo-2-fluorophenyl 2,2,2-trifluoroethyl ether, and the mixture is refluxed for 2 hours. 100 ml of petroleum ether (40–80°) are added, and the mixture is subjected to conventional work-up.

Step 4.3

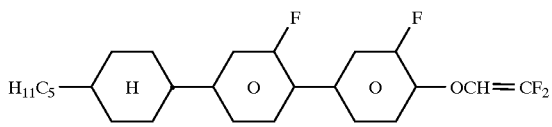

13.5 mmol of diisopropylamine are added dropwise at −20° C. to 13.5 mmol of BuLi (15% in n-hexane) in 10 ml of THF. The solution is subsequently stirred for 10 minutes and added dropwise at −40° C. under a protective gas to a mixture of 10 ml of THF and 13.5 mmol of trans-n-pentylcyclohexyl-2-fluorophenyl-2-fluorophenyl 2,2,2-trifluoroethyl ether. The mixture is stirred first at −40° C. for 0.5 hour and subsequently at room temperature overnight and then the mixture is subjected to conventional work-up. C 48 N 96.6 I, Δn=0.144; Δε8.24

The following compounds of the formula:

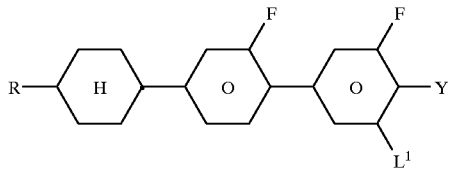

are prepared analogously to Example 3 by boronic acid coupling:

| R | Y | $L^1$ | |
|---|---|---|---|
| $C_2H_5$ | $OCH_2CF_3$ | H | |
| $C_2H_5$ | $OCH_2CF_3$ | F | |
| n-$C_3H_7$ | $OCH_2CF_3$ | F | C 84 N (79.1) I; Δn = +0.132; Δε = 14.16 |
| n-$C_4H_9$ | $OCH_2CF_3$ | H | |
| n-$C_4H_9$ | $OCH_2CF_3$ | F | |
| n-$C_5H_{11}$ | $OCH_2CF_3$ | H | |
| n-$C_5H_{11}$ | $OCH_2CF_3$ | F | C 41 N 88.9 I; Δn = +0.127; Δε = 14.29 |
| n-$C_6H_{13}$ | $OCH_2CF_3$ | H | |
| n-$C_6H_{13}$ | $OCH_2CF_3$ | F | |
| n-$C_3H_7$ | $CHF_2$ | H | |
| n-$C_3H_7$ | $CHF_2$ | F | C 73 N (31.5) I; Δn = +0.135; Δε = 14.91 |
| n-$C_5H_{11}$ | $CHF_2$ | H | |
| n-$C_5H_{11}$ | $CHF_2$ | F | C 53 N (44.8) I; Δn = +0.134; Δε = 14.18 |
| n-$C_2H_5$ | $OCH_2CF_2CHF_2$ | H | |
| n-$C_2H_5$ | $OCH_2CF_2CHF_2$ | F | C 62 N (22.5) I; Δn = +0.111; Δε = 17.7 |
| n-$C_3H_7$ | $OCH_2CF_2CHF_2$ | H | |
| n-$C_3H_7$ | $OCH_2CF_2CHF_2$ | F | C 66 N 66.7 I; Δn = +0.126; Δε = 17.94 |
| n-$C_5H_{11}$ | $OCH_2CF_2CHF_2$ | H | |
| n-$C_5H_{11}$ | $OCH_2CF_2CHF_2$ | F | C 59 N 72.1 I; Δn = +0.122; Δε = 17.07 |
| $C_2H_5$ | $OCH_2CF_2CHFCF_3$ | H | |
| $C_2H_5$ | $OCH_2CF_2CHFCF_3$ | F | C 63 I; Δn = +0.093; Δε = 19.42 |
| n-$C_3H_7$ | $OCH_2CF_2CHFCF_3$ | H | |
| n-$C_3H_7$ | $OCH_2CF_2CHFCF_3$ | F | C 59 N (47.1) I; Δn = +0.094; Δε = 19.6 |
| n-$C_5H_{11}$ | $OCH_2CF_2CHFCF_3$ | H | |
| n-$C_5H_{11}$ | $OCH_2CF_2CHFCF_3$ | F | C 35 N 51.7 I; Δn = +0.105; Δε = 18.49 |
| n-$C_3H_7$ | $OCF_2CHF_2$ | H | |
| n-$C_3H_7$ | $OCF_2CHF_2$ | F | C 68 N 102.7 I; Δn = +0.133; Δε = 11.11 |
| n-$C_5H_{11}$ | $OCF_2CHF_2$ | H | |
| n-$C_5H_{11}$ | $OCF_2CHF_2$ | F | |
| $C_2H_5$ | $OCH_2C_2F_5$ | H | |
| $C_2H_5$ | $OCH_2C_2F_5$ | F | C 36 $S_A$ (36) N 52.7 I; Δn = +0.110; Δε = 14.8 |
| n-$C_3H_7$ | $OCH_2C_2F_5$ | H | |
| n-$C_3H_7$ | $OCH_2C_2F_5$ | F | C 41 N 82 I; Δn = +0.127; Δε = 14.84 |
| n-$C_5H_{11}$ | $OCH_2C_2F_5$ | H | |
| n-$C_5H_{11}$ | $OCH_2C_2F_5$ | F | C 40 $S_B$ (15) $S_A$ (38) N 88.6 I; Δn = +0.121; Δε = 14.09 |
| n-$C_3H_7$ | $OCH_2C_3F_7$ | H | |
| n-$C_3H_7$ | $OCH_2C_3F_7$ | F | C 37 $S_B$ 27 $S_A$ 92 N 100.8 I; Δn = +0.112; Δε = 13.29 |
| n-$C_5H_{11}$ | $OCH_2C_3F_7$ | H | |
| n-$C_5H_{11}$ | $OCH_2C_3F_7$ | F | C 29 $S_B$ 47 $S_A$ 85 N 99 I; Δn =+ 0.111; Δε = 13.17 |
| $C_2H_5$ | $OCHF_2$ | H | C −2 N 44.1 I; Δn = +0.124; Δε = 10.21 |
| $C_2H_5$ | $OCHF_2$ | F | |
| n-$C_3H_7$ | $OCHF_2$ | H | C 18 N 86.4 I; Δn = +0.136; Δε = 10.79 |
| n-$C_3H_7$ | $OCHF_2$ | F | C 42 N 54.1 I; Δn = +0.130; Δε = 13.48 |
| n-$C_5H_{11}$ | $OCHF_2$ | H | C 26 N 92.7 I; Δn = +0.133; Δε = 10.14 |
| n-$C_5H_{11}$ | $OCHF_2$ | F | C 47 N 67 I; Δn = +0.124; Δε = 13.44 |
| $C_2H_5$ | $OC_2F_5$ | H | C 160 N 225.4 I; Δn = 0.125; Δε = 12.21 |
| $C_2H_5$ | $OC_2F_5$ | F | |
| n-$C_3H_7$ | $OC_2F_5$ | H | C 58 $S_B$ 69 $S_A$ 71 N 106.1 I; Δn = +0.137, Δε = 12.0 |
| n-$C_3H_7$ | $OC_2F_5$ | F | C 65 N 92.5 I; Δn = +0.128; Δε = 16.01 |
| n-$C_5H_{11}$ | $OC_2F_5$ | H | C 43 N 109.6 I; Δn = +0.127, Δε = 11.23 |
| n-$C_5H_{11}$ | $OC_2F_5$ | F | C 58 N 100.4 I; Δn = +0.124; Δε = 15.22 |
| n-$C_3H_7$ | $O(CH_2)_3CF_3$ | H | |
| n-$C_3H_7$ | $O(CH_2)_3CF_3$ | F | |
| n-$C_5H_{11}$ | $O(CH_2)_3CF_3$ | H | |
| n-$C_5H_{11}$ | $O(CH_2)_3CF_3$ | F | |
| $C_2H_5$ | $OCH=CF_2$ | H | C 24 N 41.2 I; Δn = 0.137; Δε = 8.79 |
| $C_2H_5$ | $OCH=CF_2$ | H | C 9 N 36.7 I; Δn = +0.133; Δε = 14.53 |
| n-$C_3H_7$ | $OCH=CF_2$ | H | C 35 N 90.1 I; Δn = 0.150; Δε = 8.41 |
| n-$C_3H_7$ | $OCH=CF_2$ | F | C 36 N 80.7 I; Δn = +0.146; Δε = 13.82 |
| n-$C_5H_{11}$ | $OCH=CF_2$ | F | C 21 N 90.4 I; Δn = +0.142; Δε = 13.47 |
| n-$C_3H_7$ | $OCF=CF_2$ | H | |
| n-$C_3H_7$ | $OCF=CF_2$ | F | |
| n-$C_5H_{11}$ | $OCF=CF_2$ | H | |
| n-$C_5H_{11}$ | $OCF=CF_2$ | F | |
| n-$C_3H_7$ | $CF=CF—CF_3$ | H | |

-continued

| R | Y | L¹ | |
|---|---|---|---|
| n-C$_3$H$_7$ | CF=CF—CF$_3$ | F | C 76 N 101.6 I; Δn = +0.153; Δε = 22.29 |
| n-C$_5$H$_{11}$ | CF=CF—CF$_3$ | H | |
| n-C$_5$H$_{11}$ | CF=CF—CF$_3$ | F | C 61 N 103.2 I; Δn = +0.150; Δε = 21.96 |

EXAMPLE 5

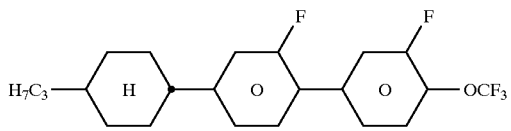

0.05 mol of 1-trifluoromethoxy-2-fluoro-4-bromobenzene and 0.05 mol of 4-(trans-4-propylcyclohexyl-2-fluorophenylboronic acid are dissolved in 125 ml of toluene and 50 ml of ethanol, and 0.6 g of tetrakis(triphenylphosphine)palladium(0) and Na$_2$CO$_3$ solution (15.9 g of Na$_2$CO$_3$ in 60 ml of H$_2$O) are added successively. The mixture is refluxed for 3 hours, and allowed to cool to room temperature, and the organic phase is separated off. The aqueous phase is extracted with toluene, and the combined organic extracts are subsequently subjected to conventional work-up. C 42 N 64.5 I; Δn=+0.125; Δε=12.55

The following compounds of the formula:

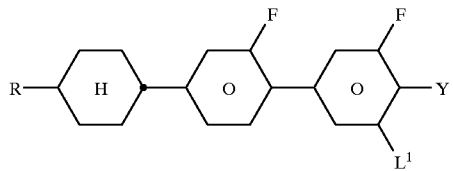

are prepared analogously

| R | Y | L¹ | |
|---|---|---|---|
| C$_2$H$_5$ | OCF$_3$ | H | C 31 N (26.6) I; Δn = +0.116, Δε = 12.07 |
| C$_2$H$_5$ | OCF$_3$ | F | C 60 I; Δn = +0.107, Δε = 16.2 |
| n-C$_3$H$_7$ | OCF$_3$ | F | C 61 N(38.4) I; Δn = +0.109, Δε = 16.11 |
| n-C$_5$H$_{11}$ | OCF$_3$ | H | C 23 N 74.2 I; Δn = +0.124, Δε = 11.55 |
| n-C$_5$H$_{11}$ | OCF$_3$ | F | C 22 N 56 I; Δn = +0.109, Δε = 15.6 |
| n-C$_6$H$_{13}$ | OCF$_3$ | H | |
| n-C$_6$H$_{13}$ | OCF$_3$ | F | |
| C$_2$H$_5$ | CF$_3$ | H | |
| C$_2$H$_5$ | CF$_3$ | F | |
| n-C$_3$H$_7$ | CF$_3$ | H | |
| n-C$_3$H$_7$ | CF$_3$ | F | C 79 I; Δn = +0.115; Δε = 22.23 |
| nC$_5$H$_{11}$ | CF$_3$ | H | |
| n-C$_5$H$_{11}$ | CF$_3$ | F | C 56 I; Δn = +0.107; Δε = 20.94 |

Mixture Examples

EXAMPLE M1

| PCH-7F | 6.0% | Clearing point [° C.]: | 75 |
|---|---|---|---|
| CCP-2OCF$_2$.F.F | 8.0% | Δn [589 nm, 20° C.]: | +0.0932 |
| CCP-3OCF$_2$.F.F | 10.0% | Δε [1 kHz, 20° C.]: | 9.5 |
| CCP-5OCF$_2$.F.F | 8.0% | V$_{(10,0,20)}$ [V]: | 1.26 |
| CCP-2OCF$_3$ | 12.0% | | |
| CCP-3OCF$_3$ | 13.0% | | |
| CCP-4OCF$_3$ | 5.0% | | |
| CCP-5OCF$_3$ | 7.0% | | |
| CGU-2-F | 15.0% | | |
| CGU-3-F | 10.0% | | |
| CGU-5-F | 6.0% | | |

EXAMPLE M2

| CCP-2OCF$_2$.F.F | 16.0% | Clearing point [° C.]: | 86 |
|---|---|---|---|
| CCP-3OCF$_2$.F.F | 11.0% | Δn [589 nm, 20° C.]: | +0.0930 |
| CCP-5OCF$_2$.F.F | 10.0% | Δε [1 kHz, 20° C.]: | 10.8 |
| CCP-2OCF$_3$.F | 15.0% | V$_{(10,0,20)}$ [V]: | 1.24 |
| CCP-3OCF$_3$.F | 11.0% | | |
| CCP-5OCF$_3$.F | 13.0% | | |
| CGU-2-F | 9.0% | | |
| CGU-3-F | 7.0% | | |
| CGU-5-F | 8.0% | | |

EXAMPLE M3

| PCH-7F | 13.0% | Clearing point [° C.]: | 64 |
|---|---|---|---|
| CCP-2OCF$_2$.F.F | 6.0% | Δn [589 nm, 20° C.]: | +0.0888 |
| CCP-3OCF$_2$.F.F | 6.0% | Δε [1 kHz, 20° C.]: | 10.8 |
| CCP-5OCF$_2$.F.F | 5.0% | V$_{(10,0,20)}$ [V]: | 1.32 |
| CCP-2OCF$_3$ | 10.0% | | |
| CCP-3OCF$_3$ | 9.0% | | |
| CCP-4OCF$_3$ | 9.0% | | |
| CCP-5OCF$_3$ | 9.0% | | |
| CGU-2-F | 11.0% | | |
| CGU-3-F | 11.0% | | |
| CGU-5-F | 11.0% | | |

EXAMPLE M4

| PCH-7F | 4.0% | Clearing point [° C.]: | 66 |
|---|---|---|---|
| CCP-2OCF$_2$.F.F | 20.0% | Δn [589 nm, 20° C.]: | +0.0950 |
| CCP-3OCF$_2$.F.F | 20.0% | Δε [1 kHz, 20° C.]: | 11.2 |
| CCP-5OCF$_2$.F.F | 20.0% | V$_{(10,0,20)}$ [V]: | 1.07 |
| CGU-2-F | 10.0% | | |
| CGU-3-F | 14.0% | | |
| CGU-5-F | 12.0% | | |

EXAMPLE M5

| PCH-7F | 4.0% | Clearing point [° C.]: | 57 |
|---|---|---|---|
| CCP-2OCF$_2$.F.F | 20.0% | Δn [589 nm, 20° C.]: | +0.0943 |
| CCP-3OCF$_2$.F.F | 19.0% | Δε [1 kHz, 20° C.]: | 10.1 |
| CCP-5OCF$_2$.F.F | 15.0% | V$_{(10,0,20)}$ [V]: | 0.97 |

-continued

| | |
|---|---|
| CGU-2-F | 16.0% |
| CGU-3-F | 14.0% |
| CGU-5-F | 12.0% |

EXAMPLE M6

| | | | |
|---|---|---|---|
| CCP-2OCF$_2$.F.F | 15.0% | Clearing point [° C.]: | 77 |
| CCP-3OCF$_2$.F.F | 12.0% | $\Delta n$ [589 nm, 20° C.]: | +0.1016 |
| CCP-2OCF$_3$ | 10.0% | $\Delta\epsilon$ [1 kHz, 20° C.]: | 10.4 |
| CCP-3OCF$_3$ | 9.0% | $V_{(10,0,20)}$ [V]: | 1.18 |
| CCP-4OCF$_3$ | 5.0% | | |
| CCP-5OCF$_3$ | 7.0% | | |
| CGU-2-F | 14.0% | | |
| CGU-3-F | 11.0% | | |
| CGU-5-F | 9.0% | | |
| BCH-3F.F | 8.0% | | |

EXAMPLE M7

| | | | |
|---|---|---|---|
| PCH-7F | 3.0% | Clearing point [° C.]: | 85 |
| CCP-2OCF$_2$.F.F | 17.0% | $\Delta n$ [589 nm, 20° C.]: | +0.0966 |
| CCP-3OCF$_2$.F.F | 16.0% | $\Delta\epsilon$ [1 kHz, 20° C.]: | 10.5 |
| CCP-5OCF$_2$.F.F | 10.0% | $V_{(10,0,20)}$ [V]: | 1.19 |
| CCP-3OCF$_2$.F | 13.0% | | |
| CCP-5OCF$_2$.F | 13.0% | | |
| CGU-2-F | 10.0% | | |
| CGU-3-F | 10.0% | | |
| CGU-5-F | 8.0% | | |

EXAMPLE M8

| | | | |
|---|---|---|---|
| PCH-7F | 3.0% | Clearing point [° C.]: | +81 |
| CCP-2OCF$_2$.F.F | 20.0% | $\Delta n$ [589 nm, 20° C.]: | +0.0872 |
| CCP-3OCF$_2$.F.F | 14.0% | $\Delta\epsilon$ [1 kHz, 20° C.]: | +9.7 |
| CCP-5OCF$_2$.F.F | 9.0% | $V_{(10,0,20)}$ [V]: | 1.25 |
| CCP-2OCF$_3$.F | 21.0% | | |
| CCP-3OCF$_3$.F | 12.0% | | |
| CCP-5OCF$_3$.F | 6.0% | | |
| CGU-2-F | 11.0% | | |
| CGU-3-F | 2.0% | | |
| CGU-5-F | 2.0% | | |

EXAMPLE M9

| | | | |
|---|---|---|---|
| PCH-7F | 3.0% | Clearing point [° C.]: | +79 |
| CCP-2OCF$_2$.F.F | 20.0% | $\Delta n$ [589 nm, 20° C.]: | +0.0873 |
| CCP-3OCF$_2$.F.F | 13.0% | $\Delta\epsilon$ [1 kHz, 20° C.]: | +9.8 |
| CCP.5OCF2.F.F | 8.0% | $V_{(10,0,20)}$ [V]: | 1.21 |
| CCP-2OCF$_3$.F | 21.0% | | |
| CCP-3OCF$_3$.F | 12.0% | | |
| CCP-5OCF$_3$.F | 7.0% | | |
| CGU-2-F | 12.0% | | |
| CGU-3-F | 2.0% | | |
| CGU-5-F | 2.0% | | |

EXAMPLE M10

| | | | |
|---|---|---|---|
| CCP-2OCF$_3$ | 2.0% | Clearing point [° C.]: | +95 |
| CCP-3OCF$_3$ | 3.0% | $\Delta n$ [589 nm, 20° C.]: | +0.1341 |
| BCH-2F.F | 10.0% | $V_{(10,0,20)}$ [V]: | 1.42 |
| BCH-3F.F | 10.0% | | |
| BCH-5F.F | 9.0% | | |
| FET-2CL | 6.0% | | |
| FET-3CL | 6.0% | | |
| CCP-3OCF$_3$.F | 10.0% | | |
| CCP-5OCF$_3$.F | 10.0% | | |
| CGU-2-F | 9.0% | | |
| CGU-3-F | 8.0% | | |
| CGU-5-F | 8.0% | | |
| CBC-33F | 5.0% | | |
| CBC-53F | 4.0% | | |

EXAMPLE M11

| | | | |
|---|---|---|---|
| CCP-2OCF$_2$.F.F | 8.0% | Clearing point [° C.]: | +64 |
| CCP-3OCF$_2$.F.F | 8.0% | $\Delta n$ [589 nm, 20° C.]: | +0.1045 |
| CCP-5OCF$_2$.F.F | 7.0% | $V_{(10,0,20)}$ [V]: | 1.04 |
| CCP-2OCF$_3$.F | 6.0% | | |
| CCP-3OCF$_3$.F | 7.0% | | |
| CCP-5OCF$_3$.F | 7.0% | | |
| CGU-2-F | 13.0% | | |
| CGU-3-F | 14.0% | | |
| CGU-5-F | 13.0% | | |
| BCH-3F.F | 4.0% | | |
| BCH-3F.F | 6.0% | | |
| BCH-5F.F | 7.0% | | |

EXAMPLE M12

| | | | |
|---|---|---|---|
| CCP-2OCF$_3$ | 4.0% | Clearing point [° C.]: | +95 |
| CCP-3OCF$_3$ | 3.0% | $\Delta n$ [589 nm, 20° C.]: | +0.1088 |
| BCH-2F.F | 5.0% | $V_{(10,0,20)}$ [V]: | 1.42 |
| BCH-3F.F | 5.0% | | |
| BCH-5F.F | 5.0% | | |
| CCP-2OCF$_3$.F | 15.0% | | |
| CCP-3OCF$_3$.F | 15.0% | | |
| CCP-5OCF$_3$.F | 15.0% | | |
| CGU-2-F | 10.0% | | |
| CGU-3-F | 9.0% | | |
| CGU-5-F | 8.0% | | |
| CBC-33F | 3.0% | | |
| CBC-53F | 3.0% | | |

EXAMPLE M13

| | | | |
|---|---|---|---|
| CCP-2OCF$_2$.F.F | 20.0% | Clearing point [° C.]: | +84 |
| CCP-3OCF$_2$.F.F | 13.0% | $\Delta n$ [589 nm, 20° C.]: | +0.0912 |
| CCP-5OCF$_2$.F.F | 7.0% | $V_{(10,0,20)}$ [V]: | 1.28 |
| CCP-2OCF$_3$.F | 21.0% | | |
| CCP-3OCF$_3$.F | 12.0% | | |
| CCP-5OCF$_3$.F | 7.0% | | |
| CGU-2-F | 12.0% | | |
| CGU-3-F | 4.0% | | |
| CGU-5-F | 4.0% | | |

EXAMPLE M14

| | | | |
|---|---|---|---|
| PCH-7F | 6.0% | Clearing point [° C.]: | 121 |
| PCH-302 | 2.0% | Δn [589 nm, 20° C.]: | +0.0903 |
| CCP-20CF$_3$ | 6.0% | V$_{(10,0,20)}$ [V]: | 1.90 |
| CGP-CF3 | 6.0% | | |
| CCP-40CF$_3$ | 6.0% | | |
| CCP-50CF$_3$ | 6.0% | | |
| ECCP-3F.F | 7.0% | | |
| ECCP-5F.F | 8.0% | | |
| CGU-3-F | 7.0% | | |
| CGU-5-F | 7.0% | | |
| CCP-30CF$_2$.F.F | 10.0% | | |
| CCP-50CF$_2$.F.F | 10.0% | | |
| CP-30CF$_3$ | 5.0% | | |
| CP-50CF$_3$ | 6.0% | | |
| CCPC-33 | 3.0% | | |
| CCPC-34 | 4.0% | | |

EXAMPLE M15

| | | | |
|---|---|---|---|
| PCH-6F | 4.0% | Clearing point [° C.]: | +113 |
| PCH-7F | 4.0% | Δn [589 nm, 20° C.]: | +0.0942 |
| CGU-5-F | 4.0% | V$_{(10,0,20)}$ [V]: | 2.07 |
| PCH-301 | 4.0% | | |
| CCP-20CF$_3$ | 4.0% | | |
| CCP-30CF$_3$ | 4.0% | | |
| CCP-40CF$_3$ | 4.0% | | |
| CCP-50CF$_3$ | 4.0% | | |
| ECCP-3F.F | 7.0% | | |
| ECCP-5F.F | 7.0% | | |
| ECCP-30CF$_3$ | 4.0% | | |
| ECCP-50CF$_3$ | 4.0% | | |
| ECCP-3F | 3.0% | | |
| ECCP-5F | 3.0% | | |
| BCH-3F.F | 3.0% | | |
| BCH-5F.F | 3.0% | | |
| CCP-20CF$_2$.F.F | 4.0% | | |
| CCP-30CF$_2$.F.F | 4.0% | | |
| CCP-50CF$_2$.F.F | 5.0% | | |
| CCP-20CF$_3$.F | 4.0% | | |
| CCP-30CF$_3$.F | 4.0% | | |
| CCP-50CF$_3$.F | 4.0% | | |
| CBC-33F | 3.0% | | |
| CBC-53F | 3.0% | | |
| CBC-55F | 3.0% | | |

EXAMPLE M16

| | | | |
|---|---|---|---|
| PCH-7F | 7.0% | Clearing point [° C.]: | +77 |
| CCH-303 | 2.0% | Δn [589 nm, 20° C.]: | +0.0906 |
| CCH-501 | 2.0% | V$_{(10,0,20)}$ [V]: | 1.40 |
| CCP-20CF$_2$.F.F | 6.0% | | |
| CCP-30CF$_2$.F.F | 6.0% | | |
| CCP-50CF$_2$.F.F | 6.0% | | |
| CCP-20CF$_3$ | 8.0% | | |
| CCP-30CF$_3$ | 9.0% | | |
| CCP-40CF$_3$ | 9.0% | | |
| CCP-50CF$_3$ | 9.0% | | |
| CGU-2-F | 11.0% | | |
| CGU-3-F | 9.0% | | |
| CGU-5-F | 9.0% | | |
| ECCP-3F.F | 3.0% | | |
| ECCP-5F.F | 4.0% | | |

EXAMPLE M17

| | | | |
|---|---|---|---|
| CGU-3-F | 10.0% | Clearing point [° C.]: | +98 |
| CGU-5-F | 10.0% | Δn [589 nm, 20° C.]: | +0.1027 |
| CCP-20CF$_3$ | 5.0% | V$_{(10,0,20)}$ [V]: | 1.34 |
| CCP-30CF$_3$ | 6.0% | | |
| CCP-40CF$_3$ | 5.0% | | |
| CCP-50CF$_3$ | 6.0% | | |
| ECCP-3F.F | 4.0% | | |
| ECCP-5F.F | 3.0% | | |
| CUP-3F.F | 10.0% | | |
| CUP-5F.F | 10.0% | | |
| CCP-20CF$_2$.F.F | 5.0% | | |
| CCP-30CF$_2$.F.F | 5.0% | | |
| CCP-50CF$_2$.F.F | 5.0% | | |
| CP-30CF$_3$ | 8.0% | | |
| CP-50CF$_3$ | 8.0% | | |

EXAMPLE M18

| | | | |
|---|---|---|---|
| CCP-2F.F.F | 13.0% | Clearing point [° C.]: | +85 |
| CCP-3F.F.F | 13.0% | Δn [589 nm, 20° C.]: | +0.0913 |
| CCP-5F.F.F | 10.0% | Δε [1 kHz, 20° C.]: | 10.9 |
| CCP-20CF$_2$.F.F | 5.0% | V$_{(10,0,20)}$ [V]: | 1.23 |
| CCP-30CF$_2$.F.F | 9.0% | | |
| CCP-50CF$_2$.F.F | 7.0% | | |
| CCP-30CF$_3$ | 11.0% | | |
| CCP-50CF$_3$ | 9.0% | | |
| CGU-2-F | 8.0% | | |
| CGU-3-F | 9.0% | | |
| CGU-5-F | 6.0% | | |

EXAMPLE M19

| | | | |
|---|---|---|---|
| CCP-20CF$_2$.F.F | 11.0% | Clearing point [° C.]: | +85 |
| CCP-30CF$_2$.F.F | 11.0% | Δn [589 nm, 20° C.]: | +0.0997 |
| CCP-50CF$_2$.F.F | 7.0% | V$_{(10,0,20)}$ [V]: | 1.24 |
| CCP-20CF$_3$.F | 11.0% | | |
| CCP-30CF$_3$.F | 12.0% | | |
| CCP-50CF$_3$.F | 15.0% | | |
| CGU-2-F | 6.0% | | |
| CGU-3-F | 10.0% | | |
| CGU-5-F | 10.0% | | |
| BCH-3F.F | 7.0% | | |

EXAMPLE M20

| | | | |
|---|---|---|---|
| CCP-2F.F.F | 11.0% | Clearing point [° C.]: | +64 |
| CCP-3F.F.F | 14.0% | Δn [589 nm, 20° C.]: | +0.0954 |
| CCP-5F.F.F | 6.0% | V$_{(10,0,20)}$ [V]: | 1.02 |
| CCP-20CF$_2$.F.F | 6.0% | | |
| CCP-30CF$_2$.F.F | 7.0% | | |
| CCP-30CF$_3$ | 8.0% | | |
| CCP-50CF$_3$ | 5.0% | | |
| CGU-2-F | 12.0% | | |
| CGU-3-F | 14.0% | | |
| CGU-5-F | 11.0% | | |
| BCH-3F.F | 6.0% | | |

EXAMPLE M21

| | | | |
|---|---|---|---|
| CCP-2F.F.F | 17.0% | Clearing point [° C.]: | +80 |
| CCP-3F.F.F | 12.0% | Δn [589 nm, 20° C.]: | +0.0874 |
| CCP-5-F.F.F | 11.0% | V$_{(10,0,20)}$ [V]: | 1.19 |
| CCP-2OCF$_2$.F.F | 6.0% | | |
| CCP-3OCF$_2$.F.F | 6.0% | | |
| CCP-5OCF$_2$.F.F | 10.0% | | |
| CCP-2OCF$_3$ | 9.0% | | |
| CCP-3OCF$_3$ | 2.0% | | |
| CCP-5OCF$_3$ | 7.0% | | |
| CGU-2-F | 10.0% | | |
| CGU-3-F | 4.0% | | |
| CGU-5-F | 6.0% | | |

EXAMPLE M22

| | | | |
|---|---|---|---|
| PCH-7F | 9.0% | Clearing point [° C.]: | +81 |
| CCH-301 | 6.0% | Δn [589 nm, 20° C.]: | +0.0734 |
| CCH-303 | 6.0% | V$_{(10,0,20)}$ [V]: | 1.72 |
| CCH-501 | 6.0% | | |
| CGU-2-F | 3.0% | | |
| CCP-2OCF$_2$.F.F | 9.0% | | |
| CCP-3OCF$_2$.F.F | 9.0% | | |
| CCP-5OCF$_2$.F.F | 13.0% | | |
| CCP-3OCF$_3$.F | 15.0% | | |
| CCP-5OCF$_3$.F | 14.0% | | |
| CP-3OCF$_3$ | 5.0% | | |
| CP-5OCF$_3$ | 5.0% | | |

EXAMPLE M23

| | | | |
|---|---|---|---|
| CCP-2.F.F.F | 13.0% | Clearing point [° C.]: | +80 |
| CCP-3.F.F.F | 13.0% | Δn [589 nm, 20° C.]: | +0.0908 |
| CCP-5.F.F.F | 10.0% | V$_{(10,0,20)}$ [V]: | 1.18 |
| CCP-2OCF$_2$.F.F | 7.0% | | |
| CCP-3OCF$_2$.F.F | 7.0% | | |
| CCP-5OCF$_2$.F.F | 7.0% | | |
| CCP-3OCF$_3$ | 11.0% | | |
| CCP-5OCF$_3$ | 7.0% | | |
| CGU-2-F | 11.0% | | |
| CGU-3-F | 8.0% | | |
| CGU-5-F | 6.0% | | |

EXAMPLE 24

| | | | |
|---|---|---|---|
| PCH-7F | 9.0% | Clearing point [° C.]: | +70 |
| CCP-2OCF$_2$.F.F | 13.0% | Δn [589 nm, 20° C.]: | +0.0855 |
| CCP-3OCF$_2$.F.F | 14.0% | Δε [1 kHz, 20° C.]: | 9.3 |
| CCP-5OCF$_2$.F.F | 15.0% | V$_{(10,0,20)}$ [V]: | 1.22 |
| CCP-2OCF$_3$.F | 17.0% | | |
| CCP-3OCF$_3$.F | 7.0% | | |
| CCP-5OCF$_3$.F | 7.0% | | |
| CGU-2-F | 10.0% | | |
| CGU-3-F | 5.0% | | |
| CGU-5-F | 3.0% | | |

EXAMPLE 25

| | | | |
|---|---|---|---|
| PCH-7F | 9.0% | Clearing point [° C.]: | +81 |
| CCP-2OCF$_2$.F.F | 20.0% | Δn [589 nm, 20° C.]: | +0.1007 |

-continued

| | | | |
|---|---|---|---|
| CCP-3OCF$_2$.F.F | 15.0% | Δε [1 kHz, 20° C.]: | 1.23 |
| CCP-5OCF$_2$.F.F | 15.0% | | |
| CCP-2OCF$_3$ | 5.0% | | |
| CCP-3OCF$_3$ | 5.0% | | |
| CGU-3-OXF | 15.0% | | |
| CGU-5-OXF | 16.0% | | |

EXAMPLE M26

| | | | |
|---|---|---|---|
| PCH-7F | 5.0% | Clearing point [° C.]: | +65 |
| CUP-2F.F | 4.0% | Δn [589 nm, 20° C.]: | +0.1066 |
| CUP-3F.F | 3.0% | Δε [1 kHz, 20° C.]: | 1.19 |
| CCP-2OCF$_3$ | 8.0% | | |
| CCP-3OCF$_3$ | 8.0% | | |
| CCP-4OCF$_3$ | 8.0% | | |
| CCP-5OCF$_3$ | 7.0% | | |
| BCH-2F.F | 8.0% | | |
| BCH-3F.F | 8.0% | | |
| BCH-5F.F | 8.0% | | |
| CGU-2-F | 11.0% | | |
| CGU-3-F | 11.0% | | |
| CGU-5-F | 11.0% | | |

EXAMPLE M27

| | | | |
|---|---|---|---|
| PCH-301 | 7.0% | Clearing point [° C.]: | +67 |
| PCH-302FF | 15.0% | Δn [589 nm, 20° C.]: | +0.0811 |
| PCH-502FF | 18.0% | Δε [1 kHz, 20° C.]: | 1.96 |
| CCP-302FF | 10.0% | | |
| CCP-502FF | 10.0% | | |
| CCP-21FF | 12.0% | | |
| CCP-31FF | 10.0% | | |
| CCH-34 | 4.0% | | |
| CCH-35 | 4.0% | | |
| CCH-301 | 5.0% | | |
| CCH-303 | 5.0% | | |

EXAMPLE M28

| | | | |
|---|---|---|---|
| CCP-3OCF$_2$.F.F | 7.0% | Clearing point [° C.]: | +72 |
| CCP-5OCF$_2$.F.F | 6.0% | Δn [589 nm, 20° C.]: | +0.1070 |
| CCP-2OCF$_3$.F | 10.0% | Δε [1 kHz, 20° C.]: | 10.7 |
| CCP-3OCF$_3$.F | 8.0% | V$_{(10,0,20)}$ [V]: | 1.12 |
| CCP-5OCF$_3$.F | 14.0% | | |
| CGU-2-F | 10.0% | | |
| CGU-3-F | 14.0% | | |
| CGU-5-F | 12.0% | | |
| BCH-2F.F | 5.0% | | |
| BCH-3F.F | 6.0% | | |
| BCH-5F.F | 8.0% | | |

EXAMPLE M29

| | | | |
|---|---|---|---|
| PCH-7F | 2.0% | Clearing point [° C.]: | +65 |
| CCP-2F.F.F | 10.0% | Δn (589 nm, 20° C.]: | +0.0936 |
| CCP-3F.F.F | 10.0% | | |
| CCP-5F.F.F | 7.0% | | |
| CCP-2OCF$_3$ | 7.0% | | |
| CCP-3OCF$_3$ | 7.0% | | |
| CCP-4OCF$_3$ | 7.0% | | |

-continued

| | |
|---|---|
| CCP-5OCF$_3$ | 7.0% |
| CGU-2-F | 14.0% |
| CGU-3-F | 13.0% |
| CGU-5-F | 13.0% |
| BCH-3F.F | 3.0% |

EXAMPLE M30

| | | | |
|---|---|---|---|
| PCH-302 | 2.0% | Clearing point [° C.]: | +93 |
| CCH-303 | 7.0% | Δn [589 nm, 20° C.]: | +0.0768 |
| CCH-501 | 7.0% | V$_{(10,0,20)}$ [V]: | 1.77 |
| CCP-2OCF$_3$ | 6.0% | | |
| CCP-3OCF$_3$ | 7.0% | | |
| CCP-4OCF$_3$ | 6.0% | | |
| CCP-5OCF$_3$ | 7.0% | | |
| ECCP-3F.F | 10.0% | | |
| ECCP-5F.F | 10.0% | | |
| CGU-3-F | 3.0% | | |
| CGU-5-F | 3.0% | | |
| CCP-2F.F.F | 10.0% | | |
| CCP-3F.F.F | 11.0% | | |
| CCP-5F.F.F | 11.0% | | |

EXAMPLE M31

| | | | |
|---|---|---|---|
| CCH-35 | 3.0% | Clearing point [°C.]: | +80 |
| CCP-2F.F.F | 6.0% | Δn [589 nm, 20° C.]: | +0.0930 |
| CCP-3F.F.F | 8.0% | Δε [1 kHz, 20° C.]: | 11.0 |
| CCP-5F.F.F | 4.0% | V$_{(10,0,20)}$ [V]: | 1.20 |
| CCP-2OCF$_2$.F.F | 14.0% | | |
| CCP-3OCF$_2$.F.F | 8.0% | | |
| CCP-5OCF$_2$.F.F | 14.0% | | |
| CCP-3OCF$_3$ | 7.0% | | |
| CCP-5OCF$_3$ | 7.0% | | |
| CGU-2-F | 10.0% | | |
| CGU-3-F | 10.0% | | |
| CGU-5-F | 9.0% | | |

EXAMPLE M32

| | | | |
|---|---|---|---|
| PCH-7F | 2.0% | Clearing point [° C.]: | +69 |
| CCP-2OCF$_2$.F.F | 20.5% | Δn [589 nm, 20° C.]: | +0.0900 |
| CCP-3OCF$_2$.F.F | 10.0% | Δε [1 kHz, 20° C.]: | 10.4 |
| CCP-5OCF$_2$.F.F | 7.0% | V$_{(10,0,20)}$ [V]: | 1.13 |
| CCP-2OCF$_3$.F | 21.0% | | |
| CCP-3OCF$_3$.F | 9.0% | | |
| CCP-5OCF$_3$.F | 3.5% | | |
| CGU-2-F | 13.0% | | |
| CGU-3-F | 9.0% | | |
| CGU-5-F | 5.0% | | |

EXAMPLE M33

| | | | |
|---|---|---|---|
| PCH-7F | 4.0% | Clearing point [° C.]: | +65 |
| CCP-2F.F.F | 10.0% | Δn [589 nm, 20° C.]: | +0.0937 |
| CCP-3F.F.F | 10.0% | V$_{(10,0,20)}$ [V]: | 1.32 |
| CCP-5F.F.F | 7.0% | | |
| CCP-2OCF$_3$ | 7.0% | | |
| CCP-3OCF$_3$ | 7.0% | | |
| CCP-4OCF$_3$ | 7.0% | | |

-continued

| | |
|---|---|
| CCP-5OCF$_3$ | 3.5% |
| CGU-2-F | 12.0% |
| BCH-2F.F | 12.0% |
| BCH-3F.F | 10.5% |
| PCH-302 | 10.0% |

EXAMPLE M34

| | | | |
|---|---|---|---|
| CCP-2F.F.F | 10.0% | Clearing point [° C.]: | +76 |
| CCP-3F.F.F | 10.0% | Δn [589 nm, 20° C.]: | +0.0936 |
| CCP-5F.F.F | 7.0% | V$_{(10,0,20)}$ [V]: | 1.32 |
| CCP-2OCF$_3$ | 7.0% | | |
| CCP-3OCF$_3$ | 7.0% | | |
| CCP-4OCF$_3$ | 7.0% | | |
| CCP-5OCF$_3$ | 4.0% | | |
| CGU-2-F | 12.5% | | |
| BCH-2F.F | 12.5% | | |
| BCH-3F.F | 12.5% | | |
| CCH-35 | 5.5% | | |
| CCH-303 | 5.5% | | |

EXAMPLE M35

| | | | |
|---|---|---|---|
| CGU-2-F | 10.0% | Clearing point [° C.]: | +10.0 |
| CGU-3-F | 10.0% | Δn [589 nm, 20° C.]: | +0.1027 |
| CGU-5-F | 10.0% | V$_{(10,0,20)}$ [V]: | 1.30 |
| CCP-2F.F.F | 5.0% | | |
| CCP-3F.F.F | 5.0% | | |
| CCP-5F.F.F | 5.0% | | |
| CCP-3OCF$_3$ | 5.0% | | |
| CCP-4OCF$_3$ | 5.0% | | |
| CCP-5OCF$_3$ | 5.0% | | |
| CCP-2OCF$_2$.F.F | 9.0% | | |
| CCP-3OCF$_2$.F.F | 8.0% | | |
| CCP-5-OCF$_2$.F.F | 8.0% | | |
| ECCP-3F.F | 6.0% | | |
| CBC-33F | 3.0% | | |
| CBC-53F | 3.0% | | |
| CBC-55F | 3.0% | | |

EXAMPLE M36

| | | | |
|---|---|---|---|
| CCP-2F.F.F | 14.0% | Clearing point [° C.]: | +59 |
| CCP-3F.F.F | 13.0% | Δn [589 nm, 20° C.]: | +0.0900 |
| CCP-5F.F.F | 8.0% | Δε [1 kHz, 20° C.]: | 11.5 |
| CCP-2OCF$_2$.F.F | 10.0% | V$_{(10,0,20)}$ [V]: | 0.97 |
| CCP-3OCF$_2$.F.F | 8.0% | | |
| CCP-3OCF$_3$ | 9.0% | | |
| CGU-2-F | 14.0% | | |
| CGU-3-F | 13.0% | | |
| CGU-5-F | 11.0% | | |

EXAMPLE M37

| | | | |
|---|---|---|---|
| CCP-2OCF$_3$ | 5.0% | Clearing point [° C.]: | +94 |
| CCP-3OCF$_3$ | 6.0% | Δn [589 nm, 20° C.]: | +0.0903 |
| CCP-4OCF$_3$ | 5.0% | V$_{(10,0,20)}$ [V]: | 1.42 |
| CCP-5OCF$_3$ | 6.0% | | |
| CGU-2-F | 6.0% | | |
| CGU-3-F | 6.0% | | |

-continued

| | |
|---|---|
| CGU-5-F | 6.0% |
| CCP-2F.F.F | 16.0% |
| CCP-3F.F.F | 16.0% |
| CCP-5F.F.F | 16.0% |
| ECCP-3F.F | 4.0% |
| ECCP-5F.F | 4.0% |
| CBC-33F | 4.0% |

EXAMPLE M38

| | | | |
|---|---|---|---|
| PCH-7F | 8.0% | Clearing point [° C.]: | +77 |
| CCH-301 | 5.0% | Δn [589 nm, 20° C.]: | +0.0729 |
| CCH-303 | 5.0% | $V_{(10,0,20)}$ [V]: | 1.59 |
| CCH-501 | 6.0% | | |
| CGU-2-F | 3.0% | | |
| CCP-2OCF$_3$ | 4.0% | | |
| CCP-3OCF$_3$ | 5.0% | | |
| CCP-4OCF$_3$ | 4.0% | | |
| CCP-5OCF$_3$ | 5.0% | | |
| CCP-2OCF$_2$.F.F | 8.0% | | |
| CCP-3OCF$_2$.F.F | 8.0% | | |
| CCP-5OCF$_2$.F.F | 11.0% | | |
| CCP-3F.F.F | 14.0% | | |
| CCP-5F.F.F | 14.0% | | |

EXAMPLE M39

| | | | |
|---|---|---|---|
| PCH-7F | 3.0% | Clearing point [° C.]: | +91 |
| PCH-302 | 4.0% | Δn [589 nm, 20° C.]: | +0.0791 |
| CCH-303 | 6.0% | $V_{(10,0,20)}$ [V]: | 1.80 |
| CCH-501 | 6.0% | | |
| CCP-2OCF$_3$ | 5.0% | | |
| CCP-3OCF$_3$ | 6.0% | | |
| CCP-4OCF$_3$ | 5.0% | | |
| CCP-5OCF$_3$ | 6.0% | | |
| ECCP-3F.F | 10.0% | | |
| ECCP-5F.F | 9.0% | | |
| CGU-3-F | 3.0% | | |
| CGU-5-F | 2.0% | | |
| CCP-2F.F.F | 8.0% | | |
| CCP-3F.F.F | 8.0% | | |
| CCP-5F.F.F | 8.0% | | |
| CCP-2OCF$_2$.F.F | 3.0% | | |
| CCP-3OCF$_2$.F.F | 3.0% | | |
| CCP-5OCF$_2$.F.F | 3.0% | | |
| CBC-33F | 2.0% | | |

EXAMPLE M40

| | | | |
|---|---|---|---|
| PCH-7F | 2.5% | Clearing point [° C.]: | 074 |
| CCH-35 | 4.0% | Δn [589 nm, 20° C.]: | +0.0871 |
| CCP-2F.F.F | 8.0% | $V_{(10,0,20)}$ [V]: | 1.27 |
| CCP-3F.F.F | 9.5% | | |
| CCP-5F.F.F | 5.0% | | |
| CCP-2OCF$_2$.F.F | 15.0% | | |
| CCP-3OCF$_2$.F.F | 10.5% | | |
| CCP-5OCF$_2$.F.F | 12.5% | | |
| CCP-3OCF$_3$ | 4.5% | | |
| CCP-5OCF$_3$ | 4.5% | | |
| CGU-2-F | 12.0% | | |
| CGU-3-F | 7.0% | | |
| CGU-5-F | 5.0% | | |

EXAMPLE M41

| | | | |
|---|---|---|---|
| PCH-7F | 4.0% | Clearing point [° C.]: | +69 |
| CCH-35 | 5.0% | Δn [589 nm, 20° C.]: | +0.0861 |
| CCP-2F.F.F | 7.0% | $V_{(10,0,20)}$ [V]: | 1.21 |
| CCP-3F.F.F | 9.0% | | |
| CCP-5F.F.F | 5.0% | | |
| CCP-2OCF$_2$.F.F | 15.0% | | |
| CCP-3OCF$_2$.F.F | 9.0% | | |
| CCP-5OCF$_2$.F.F | 13.0% | | |
| CCP-3OCF$_3$ | 3.0% | | |
| CCP-5OCF$_3$ | 3.0% | | |
| CGU-2-F | 10.0% | | |
| GGU-3-F | 10.0% | | |
| CGU-5-F | 7.0% | | |

EXAMPLE M42

| | | | |
|---|---|---|---|
| CCP-2F.F.F | 10.0% | Clearing point [° C.]: | +65 |
| CCP-3F.F.F | 10.0% | Δn [589 nm, 20° C.]: | +0.1051 |
| CCP-5F.F.F | 5.0% | $V_{(10,0,20)}$ [V]: | 1.15 |
| CCP-2OCF$_3$ | 6.0% | | |
| CCP-3OCF$_3$ | 6.0% | | |
| CCP-4OCF$_3$ | 6.0% | | |
| CCP-5OCF$_3$ | 5.0% | | |
| CGU-2-F | 14.0% | | |
| CGU-3-F | 13.0% | | |
| CGU-5-F | 13.0% | | |
| BCH-3F.F | 6.0% | | |
| FT-5.FCl | 6.0% | | |

EXAMPLE M43

| | | | |
|---|---|---|---|
| PCH-7F | 1.0% | Clearing point [° C.]: | +65 |
| CCP-2F.F.F | 10.0% | Δn [589 nm, 20° C.]: | +0.0935 |
| CCP-3F.F.F | 10.0% | $V_{(10,0,20)}$ [V]: | 1.12 |
| CCP-5F.F.F | 7.0% | | |
| CCP-2OCF$_3$ | 6.5% | | |
| CCP-3OCF$_3$ | 7.0% | | |
| CCP-4OCF$_3$ | 6.5% | | |
| CCP-5OCF$_3$ | 7.0% | | |
| CGU-2-F | 14.0% | | |
| CGU-3-F | 14.0% | | |
| CGU-5-F | 14.0% | | |
| CCP-3OCF$_2$.F.F | 3.0% | | |

EXAMPLE M44

| | | | |
|---|---|---|---|
| CCP-2F.F.F | 13.0% | Clearing point [° C.]: | +61 |
| CCP-3F.F.F | 13.0% | Δn [589 nm, 20° C.]: | +0.0909 |
| CCP-5F.F.F | 8.0% | $V_{(10,0,20)}$ [V]: | 0.99 |
| CCP-2OCF$_2$.F.F | 10.0% | | |
| CCP-3OCF$_2$.F.F | 8.0% | | |
| CCP-3OCF$_3$ | 6.0% | | |
| CCP-5OCF$_3$ | 4.0% | | |
| CGU-2-F | 14.0% | | |
| CGU-3-F | 13.0% | | |
| CGU-5-F | 11.0% | | |

EXAMPLE M45

| | | | |
|---|---|---|---|
| CCP-2F.F.F | 13.0% | Clearing point [° C.]: | +79 |
| CCP-3F.F.F | 13.0% | Δn [589 nm, 20° C.]: | 0.0910 |
| CCP-5F.F.F | 10.0% | $V_{(10,0,20)}$ [V]: | +1.18 |
| CCP-2OCF$_2$.F.F | 7.0% | | |
| CCP-3OCF$_2$.F.F | 7.0% | | |
| CCP-5OCF$_2$.F.F | 5.0% | | |
| CCP-3OCF$_3$ | 12.0% | | |
| CCP-5OCF$_3$ | 7.0% | | |
| CGU-2-F | 11.0% | | |
| CGU-3-F | 9.0% | | |
| CGU-5-F | 6.0% | | |

EXAMPLE M46

| | | | |
|---|---|---|---|
| PCH-7F | 5.5% | Clearing point [° C.]: | +79 |
| CCP-2OCF$_2$.F.F | 14.0% | Δn [589 nm, 20° C.]: | +0.0930 |
| CCP-3OCF$_2$.F.F | 9.0% | Δε [1 kHz, 20° C.]: | 11.2 |
| CCP-5OCF$_2$.F.F | 6.5% | $V_{(10,0,20)}$ [V]: | 1.16 |
| CCP-2OCF$_3$.F | 16.0% | | |
| CCP-3OCF$_3$.F | 10.0% | | |
| CCP-5OCF$_3$.F | 7.0% | | |
| CGU-2-O1DT | 16.0% | | |
| CGU-3-O1DT | 8.0% | | |
| CGU-5-O1DT | 8.0% | | |

EXAMPLE M47

| | | | |
|---|---|---|---|
| PCH-7F | 5.5% | Clearing point [° C.]: | +76 |
| CCP-2OCF$_2$.F.F | 17.0% | Δn [589 nm, 20° C.]: | +0.0925 |
| CCP-3OCF$_2$.F.F | 9.0% | Δε [1 kHz, 20° C.]: | 11.2 |
| CCP-5OCF$_2$.F.F | 6.0% | $V_{(10,0,20)}$ [V]: | 1.16 |
| CCP-2OCF$_3$.F | 18.0% | | |
| CCP-3OCF$_3$.F | 8.0% | | |
| CCP-5OCF$_3$.F | 3.0% | | |
| CGU-2-O1DT | 17.0% | | |
| CGU-3-O1DT | 8.5% | | |
| CGU-5-O1DT | 8.0% | | |

EXAMPLE M48

| | | | |
|---|---|---|---|
| PCH-5F | 2.80% | Clearing point [° C.]: | +102 |
| CCP-2OCF$_2$.F.F | 14.91% | Δε [1 kHz, 20° C.]: | 11.3 |
| CCP-3OCF$_2$.F.F | 14.00% | $V_{(10,0,20)}$ [V]: | 1.02 |
| CCP-5OCF$_2$.F.F | 14.91% | $K_1$ [$10^{-12}$ N, 20° C.]: | 10.4 |
| CUP-2F.F | 4.69% | $K_3/K_1$: | 1.40 |
| CUP-3F.F | 4.69% | | |
| CBC-33F | 4.69% | | |
| CBC-53F | 4.69% | | |
| CBC-55F | 4.62% | | |
| CGU-2-O1DT | 30.00% | | |

Comparative Example M48-1

| | | | |
|---|---|---|---|
| PCH-5F | 2.80% | Clearing point [° C.]: | +110 |
| CCP-2OCF$_2$.F.F | 14.91% | Δε [1 kHz, 20° C.]: | +11.5 |
| CCP-3OCF$_2$.F.F | 14.00% | $V_{(10,0,20)}$ [V]: | 1,11 |
| CCP-5OCF$_2$.F.F | 14.91% | $K_1$ [$10^{-12}$ N, 20° C.]: | 12.7 |
| CUP-2F.F | 4.69% | $K_3/K_1$: | 1.20 |
| CUP-3F.F | 4.69% | | |
| CBC-33F | 4.69% | | |
| CBC-53F | 4.69% | | |
| CBC-55F | 4.62% | | |
| CGU-3-O1DT | 30.00% | | |

Comparative Example M48-2

| | | | |
|---|---|---|---|
| PCH-5F | 2.80% | Clearing point [° C.]: | +113 |
| CCP-2OCF$_2$.F.F | 14.91% | Δε [1 kHz, 20° C.]: | 11.2 |
| CCP-3OCF$_2$.F.F | 14.00% | $V_{(10,0,20)}$ [V]: | 1.14 |
| CCP-5OCF$_2$.F.F | 14.91% | $K_1$ [$10^{-12}$ N, 20° C.]: | 12.9 |
| CUP-2F.F | 4.69% | $K_3/K_1$: | 1.23 |
| CUP-3F.F | 4.69% | | |
| CBC-33F | 4.69% | | |
| CBC-53F | 4.69% | | |
| CBC-55F | 4.62% | | |
| CGU-5-O1DT | 30.00% | | |

EXAMPLE M49

| | | | |
|---|---|---|---|
| PCH-5F | 4.2% | Clearing point [° C.]: | +84 |
| PCH-7F | 4.2% | Δε [1 kHz, 20° C.]: | 9.7 |
| CCP-2OCF$_3$ | 4.2% | $V_{(10,0,20)}$ [V]: | 1.08 |
| CCP-3OCF$_3$ | 5.6% | $K_1$ [$10^{-12}$ N, 20° C.]: | 10.2 |
| CCP-5OCF$_3$ | 4.9% | $K_3/K_1$: | 1.50 |
| ECCP-3F.F | 7.7% | | |
| ECCP-5F.F | 7.7% | | |
| BCH-3F.F | 4.2% | | |
| CUP-3F.F | 4.9% | | |
| CUP5F.F | 4.2% | | |
| CCP-3OCF$_2$.F.F | 4.9% | | |
| CCP-5OCF$_2$.F.F | 7.7% | | |
| CBC-33F | 2.8% | | |
| CBC-53F | 2.8% | | |
| CGU-2-O1DT | 30.0% | | |

Comparative Example M49-1

| | | | |
|---|---|---|---|
| PCH-5F | 4.2% | Clearing point [° C.]: | +92 |
| PCH-7F | 4.2% | Δε [1 kHz, 20° C.]: | 9.8 |
| CCP-2OCF$_3$ | 4.2% | $V_{(10,0,20)}$ [V]: | 1.19 |
| CCP-3OCF$_3$ | 5.6% | $K_1$ [$10^{-12}$ N, 20° C.]: | 12.5 |
| CCP-5OCF$_3$ | 4.9% | $K_3/K_1$: | 1.22 |
| ECCP-3F.F | 7.7% | | |
| ECCP-5F.F | 7.7% | | |
| BCH-3F.F | 4.2% | | |
| CUP-3F.F | 4.9% | | |
| CUP5F.F | 4.2% | | |
| CCP-3OCF$_2$.F.F | 4.9% | | |
| CCP-5OCF$_2$.F.F | 7.7% | | |
| CBC-33F | 2.8% | | |
| CBC-53F | 2.8% | | |
| CGU-3-O1DT | 30.0% | | |

Comparative Example M49-2

| | | | |
|---|---|---|---|
| PCH-5F | 4.2% | Clearing point [° C.]: | +95 |
| PCH-7F | 4.2% | Δε [1 kHz, 20° C.]: | 9.6 |
| CCP-2OCF$_3$ | 4.2% | $V_{(10,0,20)}$ [V]: | 1.21 |
| CCP-3OCF$_3$ | 5.6% | $K_1$ [$10^{-12}$ N, 20° C.]: | 12.6 |

-continued

| | | | |
|---|---|---|---|
| CCP-5OCF$_3$ | 4.9% | K$_3$/K$_1$: | 1.26 |
| ECCP-3F.F | 7.7% | | |
| ECCP-5F.F | 7.7% | | |
| BCH-3F.F | 4.2% | | |
| CUP-3F.F | 4.9% | | |
| CUP5F.F | 4.2% | | |
| CCP-3OCF$_2$.F.F | 4.9% | | |
| CCP-5OCF$_2$.F.F | 7.7% | | |
| CBC-33F | 2.8% | | |
| CBC-53F | 2.8% | | |
| CGU-5-O1DT | 30.0% | | |

EXAMPLE M50

| | | | |
|---|---|---|---|
| PCH-5F | 2.80% | Clearing point [° C.]: | 81 |
| CCP-2OCF$_2$.F.F | 14.91% | Δε [1 kHz, 20° C.]: | 10.1 |
| CCP-3OCF$_2$.F.F | 14.00% | V$_{(10,0,20)}$ [V]: | 0.98 |
| CCP-5OCF$_2$.F.F | 14.91% | K$_1$ [10$^{-12}$ N, 20° C.]: | 8.8 |
| CUP-2F.F | 4.69% | K$_3$/K$_1$: | 1.30 |
| CUP-3F.F | 4.69% | | |
| CBC-33F | 4.69% | | |
| CBC-55F | 4.69% | | |
| CGU-2-F | 30.00% | | |

Comparative Example M50-1

| | | | |
|---|---|---|---|
| PCH-5F | 2.80% | Clearing point [° C.]: | +93 |
| CCP-2OCF$_2$.F.F | 14.91% | Δε [1 kHz, 20° C.]: | 10.6 |
| CCP-3OCF$_2$.F.F | 14.00% | V$_{(10,0,20)}$ [V]: | 1.02 |
| CCP-5OCF$_2$.F.F | 14.91% | K$_1$ [10$^{-12}$ N, 20° C.]: | 9.9 |
| CUP-2F.F | 4.69% | K$_3$/K$_1$: | 1.52 |
| CUP-3F.F | 4.69% | | |
| CBC-33F | 4.69% | | |
| CBC-53F | 4.69% | | |
| CBC-55F | 4.62% | | |
| CGU-3-F | 30.00% | | |

Comparative Example M50-2

| | | | |
|---|---|---|---|
| PCH-5F | 2.80% | Clearing point [° C.]: | +98 |
| CCP-2OCF$_2$.F.F | 14.91% | Δε [1 kHz, 20° C.]: | 10.2 |
| CCP-3OCF$_2$.F.F | 14.00% | V$_{(10,0,20)}$ [V]: | 1.08 |
| CCP-5OCF$_2$.F.F | 14.91% | K$_1$ [10$^{-12}$ N, 20° C.]: | 10.7 |
| CUP-2F.F | 4.69% | K$_3$/K$_1$: | 1.40 |
| CUP-3F.F | 4.69% | | |
| CBC-33F | 4.69% | | |
| CBC-53F | 4.69% | | |
| CBC-55F | 4.62% | | |
| CGU-5-F | 30.00% | | |

EXAMPLE M51

| | | | |
|---|---|---|---|
| PCH-5F | 4.2% | Clearing point [° C.]: | +67 |
| PCH-7F | 4.2% | Δε [1 kHz, 20° C.]: | 9.0 |
| CCP-2OCF$_3$ | 4.2% | V$_{(10,0,20)}$ [V]: | 1.04 |
| CCP-3OCF$_3$ | 5.6% | K$_1$ [10$^{-12}$ N, 20° C.]: | 8.7 |
| CCP-5OCF$_3$ | 4.9% | K$_1$ [10$^{-12}$ N, 20° C.]: | 8.7 |
| ECCP-3F.F | 7.7% | K$_3$/K$_1$: | 1.27 |
| ECCP-5F.F | 7.7% | | |
| BCH-3F.F | 4.2% | | |
| CUP-3F.F | 4.9% | | |
| CUP-5F.F | 4.2% | | |
| CCP-3OCF$_2$.F.F | 4.9% | | |
| CCP-5OCF$_2$.F.F | 7.7% | | |
| CBC-33F | 2.8% | | |
| CBC-53F | 2.8% | | |
| CGU-2-F | 30.0% | | |

Comparative Example M51-1

| | | | |
|---|---|---|---|
| PCH-5F | 4.2% | Clearing point [° C.]: | +78 |
| PCH-7F | 4.2% | Δε [1 kHz, 20° C.]: | 9.5 |
| CCP-2OCF$_3$ | 4.2% | V$_{(10,0,20)}$ [V]: | 1.09 |
| CCP-3OCF$_3$ | 5.6% | K$_1$ [10$^{-12}$ N, 20° C.]: | 10.1 |
| CCP-5OCF$_3$ | 4.9% | K$_3$/K$_1$: | 1.44 |
| ECCP-3F.F | 7.7% | | |
| ECCP-5F.F | 7.7% | | |
| BCH-3F.F | 4.2% | | |
| CUP-3F.F | 4.9% | | |
| CUP-5F.F | 4.2% | | |
| CCP-3OCF$_2$.F.F | 4.9% | | |
| CCP-5OCF$_2$.F.F | 7.7% | | |
| CBC-33F | 2.8% | | |
| CBC-53F | 2.8% | | |
| CGU-3-F | 30.0% | | |

Comparative Example M51-2

| | | | |
|---|---|---|---|
| PCH-5F | 4.2% | Clearing point [° C.]: | +82 |
| PCH-7F | 4.2% | Δε [1 kHz, 20° C.]: | 9.1 |
| CCP-2OCF$_3$ | 4.2% | V$_{(10,0,20)}$ [V]: | 1.15 |
| CCP-3OCF$_3$ | 5.6% | K$_1$ [10$^{-12}$ N, 20° C.]: | 10.8 |
| CCP-5OCF$_3$ | 4.9% | K$_3$/K$_1$: | 1.41 |
| ECCP-3F.F | 7.7% | | |
| ECCP-5F.F | 7.7% | | |
| BCH-3F.F | 4.2% | | |
| CUP-3F.F | 4.9% | | |
| CUP-5F.F | 4.2% | | |
| CCP-3OCF$_2$.F.F | 4.9% | | |
| CCP-5OCF$_2$.F.F | 7.7% | | |
| CBC-33F | 2.8% | | |
| CBC-53F | 2.8% | | |
| CGU-3-F | 30.0% | | |

EXAMPLE M52

| | | | |
|---|---|---|---|
| PCH-5F | 3.2% | Clearing point [° C.]: | +104 |
| CCP-2OCF$_2$.F.F | 17.0% | Δε [1 kHz, 20° C.]: | 10.0 |
| CCP-3OCF$_2$.F.F | 16.0% | V$_{(10,0,20)}$ [V]: | 1.06 |
| CCP-5OCF$_2$.F.F | 17.0% | K$_1$ [10$^{-12}$ N, 20° C.]: | 10.2 |
| CUP-2F.F | 5.4% | K$_3$/K$_1$: | 1.74 |
| CUP-3F.F | 5.4% | | |
| CBC-33F | 5.4% | | |
| CBC-53F | 5.4% | | |
| CBC-55F | 5.3% | | |
| CGU-3-F | 20.0% | | |

Example M53

| | | | |
|---|---|---|---|
| PCH-5F | 3.60% | Clearing point [° C.]: | +11.6 |
| CCP-2OCF$_2$.F.F | 19.17% | Δε [1 kHz, 20° C.]: | 9.1 |
| CCP-3OCF$_2$.F.F | 18.00% | V$_{(10,0,20)}$ [V]: | 1.16 |
| CCP-5OCF$_2$.F.F | 19.17% | K$_1$ [10$^{-12}$ N, 20° C.]: | 10.9 |
| CUP-2F.F | 6.03% | K$_3$/K$_1$: | 1.55 |
| CUP-3F.F | 6.03% | | |
| CBC-33F | 6.03% | | |
| CBC-53F | 6.03% | | |
| CBC-55F | 5.94% | | |
| CGU-1V-F | 10.00% | | |

We claim:

1. A liquid-crystalline medium based on a mixture of polar compounds having positive dielectric anisotropy, characterized in that it contains one or more compounds of the general formula I

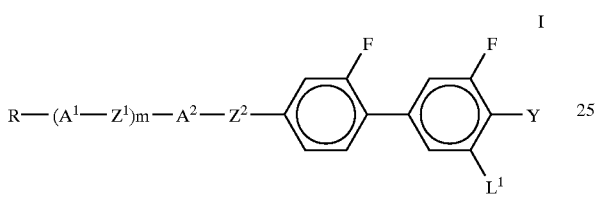

in which

R is H, an alkyl or alkenyl radical having 1 to 15 carbon atoms which is unsubstituted, monosubstituted by CN or CF$_3$ or monosubstituted by halogen, it also being possible for one or more CH$_2$ groups in these radicals to be replaced, in each case independently of one another, by —O—, —S—,

—CO—, —CO—O—, —O—CO— or —O—CO—O— in such a way that O atoms are not linked directly to one another, A$^1$ and A$^2$ are each, independently of one another, a trans-1,4-cyclohexylene radical in which, in addition, one or more non-adjacent CH$_2$ groups may be replaced by —O—, —S—, or both, or a 1,4-cyclohexenylene radical, Z$^1$ and Z$^2$ are each, independently of one another, —CO—o—, —O—CO—, —CH$_2$O—, —OCH$_2$—, —CH$_2$CH$_2$—, —CH=CH—, —C≡C— or a single bond, and one of the radicals Z$^1$ and Z$^2$ is alternatively —(CH$_2$)$_4$— or —CH=CH—CH$_2$CH$_2$—, Y is F, Cl, halogenated alkyl, alkenyl or alkoxy having 1 to 6 carbon atoms, L$^1$ is H or F, and m is 0 or 1, and one or more compounds selected from the group consisting of the general formulae II, III, IV, V and VI:

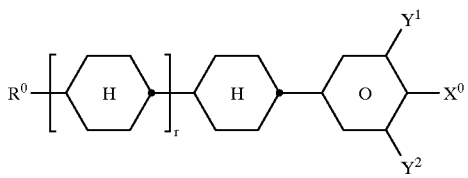

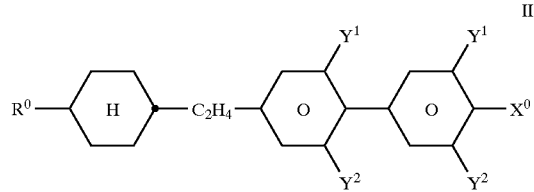

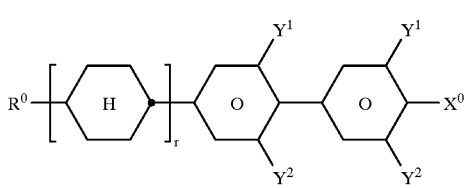

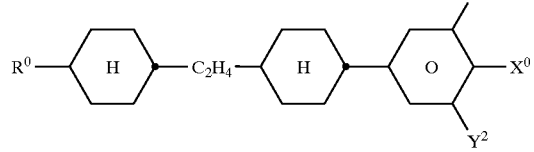

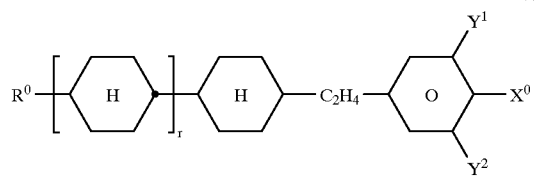

in which the individual radicals are as defined below:

R$^0$ is n-alkyl, oxaalkyl, fluoroalkyl or alkenyl, in each case having up to 7 carbon atoms, X$^0$ is F, Cl, halogenated alkyl, alkenyl or alkoxy having 1 to 6 carbon atoms, Y$^1$ and Y$^2$ are each, independently of one another, H or F, r is 0 or 1, with the provisos that a) the compounds III and IV are not identical to the compounds of the formula I, b) if L$^1$ is X m=1, A$^1$ and A$^2$ are each trans-1,4cyclohexylene radicals, Z$^1$ is a single bond and Z$^2$ is —CH$_2$CH$_2$—, then Y is not Cl, c) if L$^1$ H, m=0, A$^2$ is a trans 1,4-cyclohexylene radical and Z$^1$ is —CH$_2$CH$_2$—, then Y is not F, Cl, —CF$_3$, —OCHF$_2$, —CHF$_2$ or —OCF$_3$, e) if Y$^1$ and Y$^2$ on the central phenylene ring of formula IV are F, r of formula IV is 1, Z$^2$ of formula I is a single bond, and m=0, then Y is halogenated alkyl, alkenyl or alkoxy having 2–6 carbon atoms.

2. Medium according to claim 1, characterized in that the proportion of compounds of the formulae I to VI together is at least 50% by weight in the total mixture.

3. Medium according to claim 1, characterized in that the proportion of compounds of the formula I is from 3 to 80% by weight in the total mixture.

4. Medium according to claim 1, characterized in that the proportion of compounds of the formulae II to VI is from 20 to 80% by weight in the total mixture.

5. Medium according to claim 1, characterized in that it contains a compound of the formula

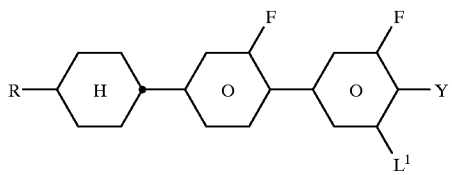

in which R, $L^1$ and Y are as defined in claim 1.

6. Medium according to claim 5, characterized in that Y is F, $OCHF_2$ or $OCF_3$.

7. Medium according to claim 1, characterized in that R in the compounds of the formula I is selected from the group consisting of ethyl, propyl and pentyl.

8. Medium according to claim 1, characterized in that it contains one or more compounds of the formula I and one or more compounds of the formula

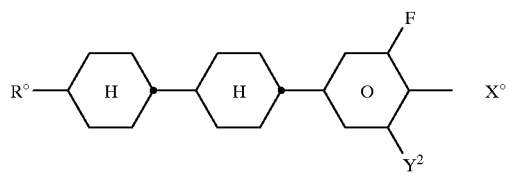

in which $X^0$ is F, $OCF_3$ or $OCHF_2$, $R^0$ is n-alkyl, oxaalkyl, fluoroalkyl or alkenyl, in each case having up to 9 carbon atoms, and $Y^2$ is H or F.

9. A method of using the liquid-crystalline medium according to claim 1 which comprises incorporating said liquid-crystalline medium into an electrooptical device.

10. Electrooptical liquid-crystal display containing a liquid-crystalline medium according to claim 1.

11. Compounds of the formula I

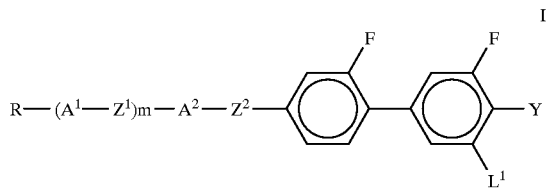

in which R, $A^1$, $A^2$, $Z^1$, $Z^2$, and m are as defined in claim 1, and $L^1$ is H and Y is halogenated alkyl, alkenyl or alkoxy having 2–6 carbon atoms.

12. Compounds of the formula

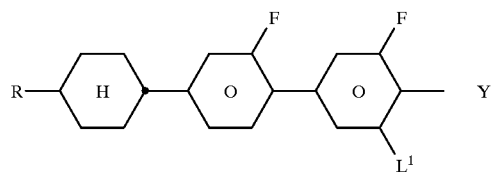

in which R, Y and $L^1$ are as defined in claim 1.

13. A liquid-crystalline medium based on a mixture of polar compounds having positive dielectric anisotropy, characterized in that it contains one or more compounds of the general formula I

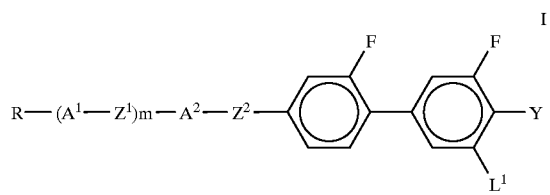

in which

R is H, an alkyl or alkenyl radical having 1 to 15 carbon atoms which is unsubstituted, monosubstituted by CN or $CF_3$ or monosubstituted by halogen, it also being possible for one or more $CH_2$ groups in these radicals to be replaced, in each case independently of one another, by —O—, —S—,

,

—CO—, —CO—O—, —O—CO— or —O—CO—O— in such a way that O atoms are not linked directly to one another, $A^1$ and $A^2$ are each, independently of one another, a trans-1,4-cyclohexylene radical in which, in addition, one or more non-adjacent $CH_2$ groups may be replaced by —O—, —S—, or both, or a 1,4-cyclohexenylene radical, $Z^1$ and $Z^2$ are each, independently of one another, —CO—o—, —O—CO—, —$CH_2$O—, —O$CH_2$—, —$CH_2CH_2$—, —CH=CH—, —C≡C— or a single bond, and one of the radicals $Z^1$ and $Z^2$ is alternatively —$(CH_2)_4$— or —CH=CH—$CH_2CH_2$—, Y is F, Cl, halogenated alkyl, alkenyl or alkoxy having 1 to 6 carbon atoms, $L^1$ is H or F, and m is 0 or b 1, and one or more compounds selected from the group consisting of the general formulae II, III, IV, V and VI:

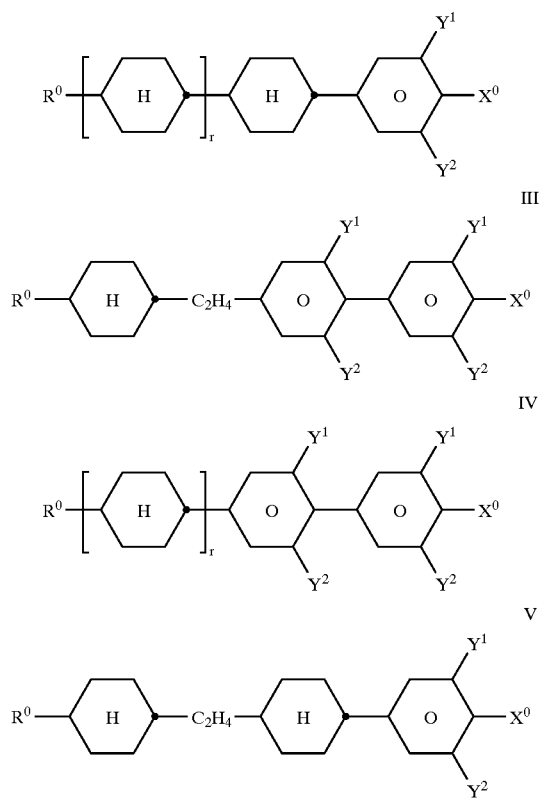

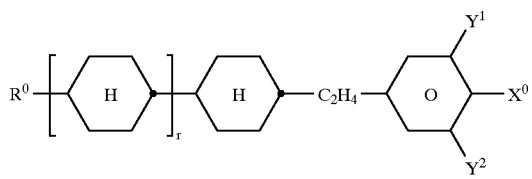

in which the individual radicals are as defined below:

$R^0$ is n-alkyl, oxaalkyl, fluoroalkyl or alkenyl, in each case having up to 7 carbon atoms, $X^0$ is F, Cl, halogenated alkyl alkenyl or alkoxy having 1 to 6 carbon atoms, $Y^1$ and $Y^2$ are each, independently of one another, H or F, r is 0 or 1, with the provisos that a) the compound III and IV are not identical to the compounds of the formula I, b) if $L^1$ is H, m=1, $A^1$ and $A^2$ are each trans-1,4-cyclohexylene radicals, $Z^1$ is a single bond and $Z^2$ is $CH_2C_2$—, then Y is not Cl, c) if $L^1$ is H, m=0, $A^2$ is a trans-1,4-cyclohexylene radical and $Z^2$ is —$CH_2CH_2$—, then Y is not F, Cl, —$CF_3$, —$OCHF_2$, —$CHF_2$ or —$OCF_3$, and d) if $Y^1$ and $Y^2$ on the central phenylene ring of formula IV are F, and r is 1, then Y is halogenated alkyl, alkenyl or alkoxy having 2–6 carbon atoms.

* * * * *